(12) United States Patent
van Bommel et al.

(10) Patent No.: US 7,645,805 B2
(45) Date of Patent: *Jan. 12, 2010

(54) GELLING AGENTS

(75) Inventors: Kjeld Jacobus Cornelis van Bommel, Groningen (NL); Johannes Henricus van Esch, Groningen (NL); Maaike de Loos, Groningen (NL); André Heeres, Groningen (NL); Bernard Lucas Feringa, Paterswolde (NL)

(73) Assignee: Applied Nanosystems, B.V., Groningen (NL)

( * ) Notice: Subject to any disclaimer, the term of this patent is extended or adjusted under 35 U.S.C. 154(b) by 590 days.

This patent is subject to a terminal disclaimer.

(21) Appl. No.: 10/515,209

(22) PCT Filed: May 22, 2003

(86) PCT No.: PCT/NL03/00381

§ 371 (c)(1),
(2), (4) Date: Jun. 8, 2005

(87) PCT Pub. No.: WO03/097587

PCT Pub. Date: Nov. 27, 2003

(65) Prior Publication Data

US 2005/0250857 A1      Nov. 10, 2005

(30) Foreign Application Priority Data

May 22, 2002   (EP) .................................. 02077007

(51) Int. Cl.
*C08J 3/075* (2006.01)
*A61K 9/10* (2006.01)

(52) U.S. Cl. ........................ 516/103; 516/125; 516/126; 516/129; 516/130; 516/131; 516/132; 516/133; 424/489; 424/499

(58) Field of Classification Search .................. 516/103, 516/125–133; 424/489, 499
See application file for complete search history.

(56) References Cited

U.S. PATENT DOCUMENTS

| 4,118,418 | A |   | 10/1978 | Conrow et al. |
| 4,515,920 | A |   | 5/1985 | Erickson |
| 5,338,725 | A | * | 8/1994 | Ojima et al. .................. 514/13 |
| 6,096,710 | A | * | 8/2000 | Goodman et al. ............. 514/17 |
| 2005/0272677 | A1 | * | 12/2005 | Friesen et al. .................. 514/44 |
| 2006/0099270 | A1 | * | 5/2006 | Friggeri et al. ............... 424/489 |

FOREIGN PATENT DOCUMENTS

| JP | 2000 072736 | 3/2000 |
| WO | WO 00/35998 | 6/2000 |
| WO | WO 03/097587 A2 | 11/2003 |

OTHER PUBLICATIONS

Brzezinski et al., "Model Molecules for the Active Centre of Alcoholdehydrogenases—An FT-IR Study", Biochemical and Biophysical Research Communications 231, 473-476 (1997).*
Feng et al., "Collagen-Based Structures Containing the Petoid Residue N-Isobutylglycine (Nleu): Synthesis and Biophysical Studies of Gly-Pro-Nleu Sequences by Circular Dichroism, Ultraviolet Absorbance, and Optical Rotation", Biopolymers, 39, 859-872 (1996).*
Kirk-Othmer, Encyclopedia of Chemical Technology, Fourth Edition, John Wiley & Sons, 1995, pp. 829-837.*
Morrison-Boyd, Organic Chemistry, Third Edition, Allyn and Bacon, Inc., 1973, pp. 294-308.*
David K. Leung, et al., Synthesis and Binding Properties of Cyclodextrin Trimers, Tetrahedron Letters 42 (2001) pp. 6255-6258.
Kent E. Pryor, et al., The Activated Core Approach to Combinatorial Chemistry: A Selection of New Core Molecules, Tetrahedron 54 (1998) pp. 4107-4124.
Hideki Fujii, et al., Antimetastatic Activities of Synthetic ARG-GLOY-ASP-SER (RGDS) and -ARG-LEU-ASP-SER . . . , Biol. Pharm. Bull. 18(12) pp. 1681-1688 (1995) XP-001108987.
P. Muller, et al., Tethering of Long-Chain Amino Acids to a Rigid Aromatic Core-A New Type of Preorganized . . . Journal of Surfactants and Detergents, vol. 4, No. 4 (Oct. 2001) XP-001108875.
Frank Sinner, et al., A New Class of Continuous Polyer Supports Prepared by Ring-Opening Metathesis Polymerization: . . . Macromolecules, 2000, 33, pp. 5777-5786 XP-002217867.
Drew S. Pche, et al., Crosslinking of Poly . . . Plymer Bulletin 43, pp. 43-49 (1999) XP-002217866.
Database Caplus, Online! Chemical Abstracts Service, Columbus, Ohio, US 2000, XP002217710.
Database Caplus, Online! Chemical Abstracts vol. 132, No. 15, Apr. 3, 2000, abstract No. 194655, XP002217709.
Darshan Ranganathan, et al., Design and Synthesis of . . . , 2000 John Wiley Sons, Inc., Biopoly 54: 289-295, XP001040555.
Sinan H. Battach, et al., Synthesis and Biological Studies of 5-Aminolevulinic . . . , Bioconjugates Chem. 2001, 12, pp. 980-988, XP001092540.

* cited by examiner

*Primary Examiner*—Douglas McGinty
(74) *Attorney, Agent, or Firm*—Lucas & Mercanti, LLP

(57) ABSTRACT

The invention relates to a novel class of gelling agents, to a process of preparing said agents, to the use of said agents to prepare gels, and to the gels thus obtained. A gelling agent or thickener according to the invention comprises a core which is functionalized with three amino acid derived groups by means of an amide or urea linkage. It may be used to gelate or thicken numerous solvents.

29 Claims, No Drawings

GELLING AGENTS

This patent application claims the benefit of priority from European Patent Application No. EP 02077007.9 filed May 22, 2002 through PCT Application Serial No. PCT/NL2003/000381 filed May 22, 2003, the contents of each of which are incorporated herein by reference.

The invention relates to a novel class of gelling agents, to a process of preparing said agents, to the use of said agents to prepare gels, and to the gels thus obtained.

Thermally reversible gelling or thickening of organic solvents or water by low molecular weight compounds is of particular interest for hardening of spilled fluids and cooking oils, thickening of paints, cosmetic materials and several other technical applications. The self assembly of these gelator/thickener molecules occurs by means of non-covalent interactions such as hydrophobic interaction, π-π interactions, electronic interactions, hydrogen bonding or combinations thereof. Although several gelator/thickener molecules have been identified during the last decade, there is still interest in stable gelator/thickeners that can be synthesized easily from cheap, renewable sources and gelate or thicken a wide variety of solvents.

The present invention aims to provide a novel class of gelling agents or thickeners. It is an object of the invention to provide gelling agents or thickeners that are based on readily available and economically attractive starting materials. It is further an object of the invention to provide gelling agents or thickeners that are capable of gelling or thickening a wide variety of solvents making the gelling agents or thickeners suitable to be employed in various applications. Other objects of the invention will become clear from the discussion of the invention and a number of its embodiments presented below.

Surprisingly, it has been found that the above objects can be reached by preparing gelling agents or thickeners from no acids, oligopeptides or derivatives thereof. A gelling agent or thickener according to the invention comprises a core which is functionalized with three no acid derived groups by means of an amide or urea linkage. These groups may be the same or different, however, it is preferred that these three groups are the same.

Accordingly, the invention relates to a gelling agent having the formula

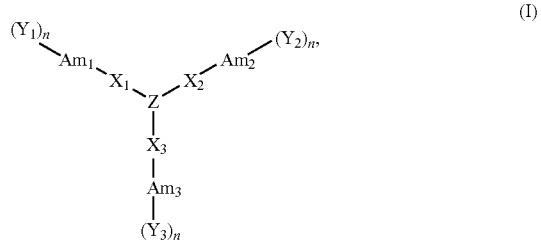

(I)

wherein

Z represents a cycloalkyl, a heterocycloalkyl, an aromatic or heteroaromatic moiety;

each of $X_1$, $X_2$ and $X_3$ is independently chosen from the moieties —NH, C(O)—, and —NH—C(O)—;

each of $Am_1$, $Am_2$, and $Am_3$ is independently a moiety based on an amino acid or a derivative thereof, or a number of amino acids or derivatives thereof, each of $Y_1$, $Y_2$, and $Y_3$ is independently chosen from the group of —OR, —N(OH)R, and —NR$_2$, if the corresponding X ($X_1$ for $Y_1$, $X_2$ for $Y_2$, and $X_3$ for Ys) is —C(O)— or —NH—C(O)— and n=1, and each of $Y_1$, $Y_2$, and $Y_3$ is independently chosen from the group of C(O)R, —C(O)—NR$_2$, —C(O)—OR, —C(S)R, —C(S)—NR$_2$, —C(S)—OR and R, if the corresponding X ($X_1$ for $Y_1$, $X_3$ for $Y_2$, and 14 for $Y_3$) is —NH— and n=1 or 2, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms; and n is 1 or 2.

It has been found that a gelling agent or thickener according to the invention is not only useful for gelation or thickening of organic solvents or water, but they also can be used as a chromatographic support for chiral recognition or a precursor therefore (separation of enantiomers, see e.g. G. Gubitz et al., *Biopharm. Drug Dipos.* 22 (2001) 291-386), and immobilization of catalysts.

Ranganathan et al. have disclosed in *Biopolymers*, 64 (2000) 289-295 crystal information of peptide dendrimers based on a benzene core to which branched structures of oligopeptides are connected. All disclosed compounds are based on glutamine as only amino acid in the oligopeptides. It is mentioned that third generation dendrimers do not crystallize, but form gels. However, lower generation dendrimers crystallize.

The international application 00/35998 discloses gelators for carbon dioxide, which may be based on amino acids. Nothing is mentioned about gelation of other media. The disclosed compounds are highly fluorinated, which makes them less suitable for gelation or thickening of polar media, particularly aqueous media.

JP 2000 072736 discloses benzene tricarboxamides and their use as solidifying agent for waste oils, diesel fuel, lubricant oils and the like. The substituents to the benzene groups contain an —NHR group attached to an amino acid residue, in which R is an alkyl group from 8 to 22 carbon atoms. These groups are relatively apolar and bulls, making the disclosed benzene tricarboxamides less suitable for gelation or thickening of polar media, particularly aqueous media.

In the context of the invention, a cycloalkyl group is defined as a saturated or unsaturated cyclic alkyl group having from 4 to 18 carbon atoms. Preferred are cycloalkyl groups comprising 6- or 6-membered rings, i.e. cyclopentyl, cyclopentadienyl or cyclohexyl groups. It is to be noted that also annulated multiple ring systems are encompassed by the term cycloalkyl group. Examples are decahydranaphtalene, dodecahydraphenalene, and hexadecahydropyrene.

A heterocycloalkyl group is defined as a saturated or unsaturated cyclic alkyl group having one or more heteroatoms (i.e. atoms other than carbon atoms) in the ring. The heterocycloalkyl group preferably comprises one or more fused or coupled 4- to 16-, more preferably 5- or 6-membered ring. Preferred heteroatoms that can be present in the ring are oxygen, sulfur and nitrogen. It is preferred that one or two heteroatoms are present in the ring. These may be the same or different. It is to be noted that also annulated multiple ring systems are, encompassed by the term heterocycloalkyl group. Examples are tetrahydropyran, tetrahydrothiopyran, dioxane, trans-hexahydro-isochroman, and trans-hydro-isothiochroman.

An aromatic group is defined as a cyclic group having an aromatic character comprising from 6 to 18 carbon atoms wherein the ring system(s) only contains carbon atoms. It is to be noted that also fused or coupled multiple ring systems are encompassed by the term aromatic group. Examples are phenyl, naphtyl, anthracyl and pyrene.

A heteroaromatic group is an aromatic group wherein one or more carbon atoms in a ring have been replaced by a heteroatom. Preferred heteroatoms that can be present in the ring are oxygen, sulfur and nitrogen. It is preferred that one or two heteroatoms are present in the ring. These may be the same or different. It is to be noted that also fused or coupled multiple ring systems are encompassed by the term heteroaromatic group. Examples are furan, pyridine, pyrazine, quinoline, and thiophene.

It is preferred that Z represents a cyclohexyl or phenyl group. Preferably, the cyclohexyl or phenyl group is 1,3,5-substituted by the X—Am—Y groups. In a more preferred embodiment, Z represents a 1,3,5-substituted cyclohexyl group.

$X_1$, $X_2$ and Xs each can be a —NH—, a —C(O)—, or a —NH—C(O)— group. Accordingly, the $Am_1$, $Am_2$, and $Am_3$ groups can each independently be connected to Z by attachment to a C=O or a NH group. The choice for each $X_1$, $X_2$ and $X_3$ will depend on whether the respective $Am_1$, $Am_2$, and $Am_3$ groups are to be attached at their $NH_2$-terminus or their COO-terminus. If an amino acid or oligopeptide is connected through its $NH_2$-terminus, the particular $X_1$, $X_2$ or $X_3$ will be —C(O)— or —NH—C(O)—. Likewise, if an amino acid or oligopeptide is connected through its COOH-terminus the particular $X_1$, $X_2$ or Xs will be an NH group.

Each $Am_1$, $Am_2$, and $Am_3$ group is based on an amino acid or a derivative thereof. In principle, any group comprising at least one —NH or —$NH_2$ group and at least one —COOH group is considered an amino acid. It will be understood that each $Am_1$, $Am_2$, and $Am_3$ does not represent a complete amino acid. The amino acids are connected either through their $NH_2$-terminus to a corresponding X group and through their COOH-terminus to a corresponding Y group, or vice versa. Each connection is an amide bond. Accordingly, an H of the $NH_2$-terminus, and the —OH of the COOH-terminus are not part of the overall structure.

It is also possible that these groups are based on more than one amino acid or a derivative thereof and accordingly comprise a di-, tri-, or oligopeptide. Preferably, each oligopeptide is based on up to 12, preferably 2 to 5 amino acids, forming a linear peptide chain in which the amino acids are connected head-to-tail to one another. The amino acids may be chosen from all natural and unnatural (synthetic, e.g. β-amino acids or α-alkylated amino acids) amino acids. Preferably, the amino acids are α, β, or γ-amino acids, of which both the d and the l isomers are eligible. Particularly preferred are α-amino acids. Suitable examples of amino acids are leucine, isoleucine, lysine, valine, proline, methionine, glycine, histidine, alanine, phenylalanine, tryptophan, serine, threonine, cysteine, tyrosine, asparagine, glutamine, aspartic acid, glutamic acid, and arginine. In the context of the invention, a derivative of an amino acid is defined as to include esters or amides (e.g. of aspartic acid, lysine or glutamic acid) and (thio)ethers (e.g. of serine, tyrosine or cysteine).

Each amino acid may be substituted with a substituent, wherein each substituent may be a substituted or unsubstituted, branched, cyclic or straight alkyl or alkenyl group which possibly contains an aromatic, ester or ether moiety or one or more other heteroatoms chosen from the group of N, S, O, P and B. Preferably, each substituent does not contain more than 12 carbon atoms. Preferably, each of Am1, Am2 and Am3 contains none or one substituent.

The end groups $Y_1$, $Y_2$ and $Y_3$ each may independently be chosen from the groups dependent on the nature of the corresponding X ($X_1$ for $Y_1$, $X_2$ for $Y_2$, and Xs for Ys) and the value of n. For instance, if $X_1$ is —C(O)— or —NH—C(O)— and n=1, $Y_1$ may be —OR, —N(OH)R, and —$NR_2$. If $X_2$ is for instance —NH— and n=2, $Y_2$ may be —C(O)R, —C(O)—$NR_2$, —C(O)—OR, —C(S)R, —C(S)—$NR_2$, —C(S)—OR and R. In the latter case, two $Y_1$, $Y_2$ or $Y_3$ groups may be interconnected by an R-group, not being H. Each of the R-groups mentioned in this regard, may be independently chosen from the group of H and substituted or unsubstituted, branched, cyclic or straight alkyl, alkenyl or alkynyl groups which possibly contain an aromatic, ester or ether moiety or one or more other heteroatoms and may have from 1 to 40 carbon atoms, but preferably has less than 8 carbon atoms. It is preferred that each R-group contains one or more heteroatoms chosen from O, N, S, P and B.

Preferably, $Y_1=Y_2=Y_3=$ —OH, —$OCH_3$, —$OCH_2CH_3$, —$OCH_2CH_2OH$, —$NH_2$, —$NHCH_2CH_2OCH_2CH_2OH$, —$OCH_2CH_2OCH_2CH_3$, —$OCH_2CH_2OCH_2CH_2OH$, —NHOH, —$NHCH_3$, —NH—$CH_2$-p-$C_6H_4$—$B(OH)_2$, or —$NHCH_2CH_2OH$.

In one embodiment, R contains a terminal reactive group, such as an alkenyl group. By choosing an appropriate terminal reactive group, a gelling agents or thickener according to the invention may be used to form a a gel which can be subjected to further reaction. For instance, a gelling agent or thickener with a terminal alkenyl group (C=C) can, after formation of a viscous solution in au aromatic solvent be interconnected by a metathesis reaction following standard procedures as found in e.g. *J. Am. Chem. Soc.* (1995) 117, 12364. The metathesis reaction transforms the viscous solution into a stiff gel, which can for instance be used in columns for chromatographic purposes (see also Sinner et al., *Angew. Chem. Int. Ed.* 39 (2000) 1433-1436 and Sinner et al., *Macromolecules* 33 (2000) 5777-5786).

A gelling agent or thickener according to the invention can be prepared by reaction of an appropriate substituted cycloalkyl heterocycloalkyl, aromatic or heteroaromatic compound, such as 1,3,5-triaminobenzene, 1,3,5-tri(chlorocarbonyl)cyclohexane or 1,3,5-tri(chlorocarbonyl)benzene, or 1,3,5-triaminocyclohexane, or 1,3,5-benzene triisocyanate, with a pre-prepared, optionally activated amino acid or di-, tri-, or oligopeptide derivative, such as an amino acid awl ester, an amino acid alkyl amide, an amino acid glycol ester or an amino acid glycol amide. Feasible reactions and their conditions may be based on standard synthetic methods for amide and urea formation as described in M. B. Smith, J. March, *March's Advanced Organic Chemistry*, 2001, 5th edition, Wiley Interscience, and E. Muller, O. Bayer, *Houben-Weyl, Methoden der Organischen Chemie, Synthesen von Peptiden*, Band XV/1 and 2, 1974, George Thieme Verlag.

Typical methods of preparing a gelling agent or thickener according to the invention will now be described with reference to six preferred groups of compounds. It will be understood by the skilled person that many variations in the synthesis are possible without leaving the scope of the invention.

Group 1

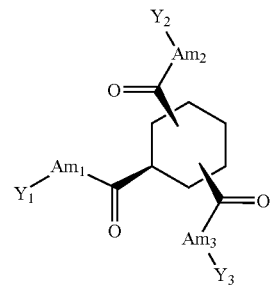

(◂ represents a substituent in an equatorial position of the cyclohexane core)

A thickener or gelling agent according to this formula can be prepared by reaction of a cyclohexanetricarboxylic acid with $SOCl_2$ (formation of the acyl chloride) and subsequent reaction (K. Hanabusa, A. Kawakima, M. Kimura, H. Shirai, *Chem. Lett* (1997) 191-192) with a free amino group of an amino acid derivative, such as an amino acid allyl ester or amide or an amino acid glycol ester or amide (according to standard organic procedures for amide and ester formation [of amino acids] as described in a.o. M. Kunishama, C. Kawachi, J. Morita, K Tereao, F. Iwasaki, S. Tani, *Tetrahedron* (1999)

13159-13170; M. B. Smith, J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans.* 2, (1996) 2707-2713; H. Tamiaki, A Kiyomori, K. Maruyama, *Bull. Chem. Soc. Jpn*, 66, (1993) 1768-1772; S. Bhattacharya, S. N. G. Acharya, *Chem. Mater.* (1999) 3121-3132).

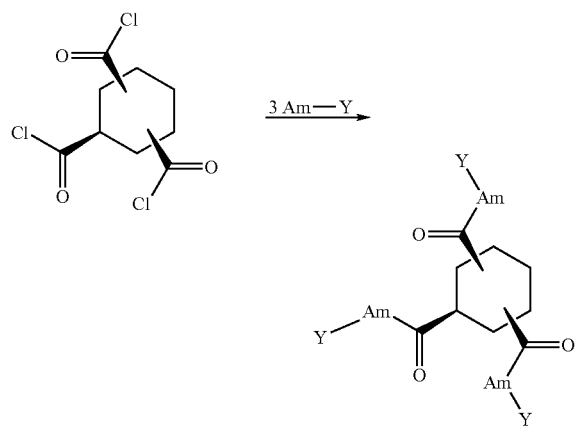

(◂ represents a substituent in an equatorial position of the cyclohexane core)

Y=OH can be prepared easily from Y=OR' by hydrolysis under alkaline conditions

Group 2

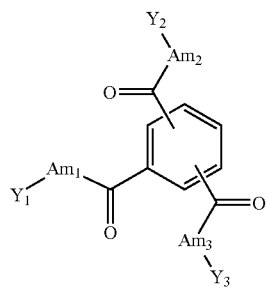

A thickener or gelling agent according to this formula can be prepared by reaction of a benzenetricarboxylic acid with SOCl$_2$ (formation of the acyl chloride) and subsequent reaction (K. Hanabusa, A. Kawakima, M. Kimura, H. Shirai, *Chem. Lett* (1997) 191-192) with a free amino group of an amino acid derivative, such as an amino acid alkyl ester or amide or an aminoacid glycol ester or amide.

Group 3

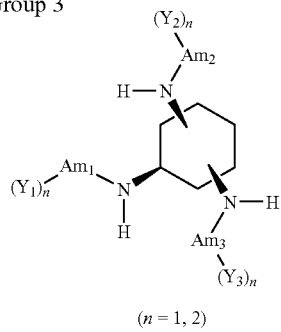

$(n = 1, 2)$ (◂ represents a substituent in an equatorial position of the cyclohexane core)

A thickener or gelling agent according to this formula can be prepared by reaction of a triaminocyclohexane (T. Bowen, R. P. Planalp, M. W.

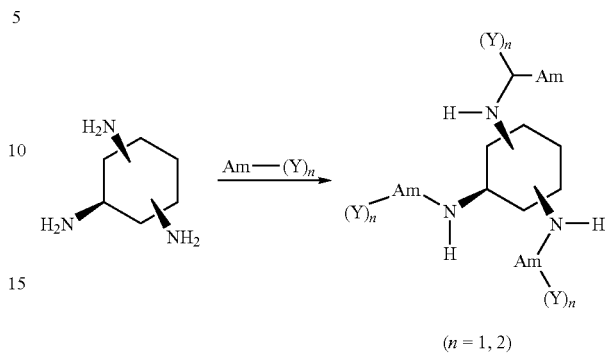

$(n = 1, 2)$

Brechbiel, *Bioorg. Med. Chem. Lett.* (1996) 807-810) with the flee or activated arboxylic acid moiety of a) an amino acid protected at the N-terminus; e.g. NH(CO)—R (J. March, *March'e Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Bam-d XV/1 and 2, 1974, George Thieme Verlag), NH(CO)OR(H-J. Knolker, T. Braxmeier, *Synlett.* (1997) 925-928, J. S. Nowick, D. L. Holmes, G. Noronha, E. M. Smith, T. M. Nguyen, S-L. Huang, *J. Org. Chem.*, (1996) 3929-3934, 1. Vauthey. F. Valot, C. Gozzi F. Fache, M. Lemaire, *Tetrahedron Lett.* (2000) 6347-6350), S. Gasataldi, S. M. Weinreb, D. Stein, *J. Org. Chem.* (2000), 3239-3249, D. C. D. Butler, H. Alper, *Chem. Commun.* (1998) 2575-2576, P. Maier, R. S. Randad, J. Org. Chem., (1994) 1987-1938, R. A. Batey, V. Santhakumar, C. Yoshinashi, S. D. Taylor, *Tetrahedron Lett.* (1998) 6267-6270, S. M. Hutchins, K. T. Capman, *Tetrahedron Lett.* (1995) 2583-2586.

b) an amino acid in which the free ne is reacted with an aldehyde (formation of an imine); N=C—R (J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Band XV/1 aid 2, 1974, George Thieme Verlag).

Group 4

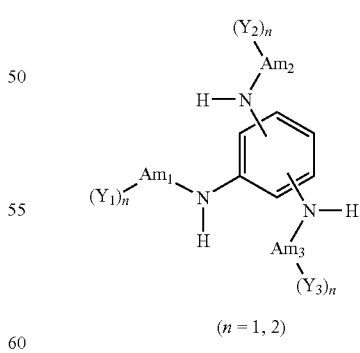

$(n = 1, 2)$

A thickener or gelling agent according to this formula can be prepared by reaction of a benzenetriamine (T. Yamaoka, H. Hosoya, S. Nagakura, *Tetrahedron* (1968) 6203-6213) with the free or activated carboxylic acid moiety of an amino acid derivative (see compounds of Group 3), or other simple C—N forming protocols (transition metal amination of aryl iodides)

B. H. Yang, S. L. Buchwald, *Organometal. Chem.* (1999) 125-146, J. F. Hartwig, *Angew. Chem. Int. Ed Engl.* (1998) 2046-2067.

Group 5

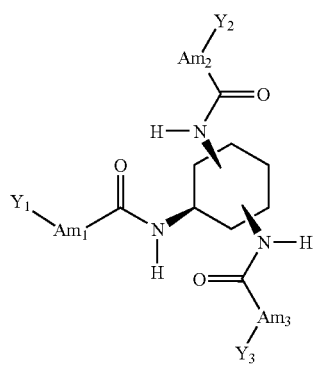

(◂ represents a substituent in an equatorial position of the cyclohexane core)

A thickener or gelling agent according to this formula can be prepared by activation of the triaminocyclohexane with phosgene, triphosgene, carbonyldiimidazole or (4-nitro)phenyl carbamate and subsequent reaction with a free amino group (G. T. Wang, Y. W. Chen, S. D. Wang, R. Sciotti, *Tetrahedron Lett.* (1997) 1895-1898, P. Majer, R. S. Randad, *J. Org Chem.*, (1994) 1937-1938, R. A. Batey, V. Santhakumar, C. Yoshinashi, S. D. Taylor, *Tetrahedron Lett.* (1998) 6267-6270, S. M. Hutchins, K. T. Capman, *Tetrahedron Lett.* (1995) 2583-2586) of an amino acid derivative, such as an amino acid alkyl ester or amide or an amino acid glycol ester or amide. It is often assumed that the second step takes place via the formation of an isocyanate.

In another embodiment the cyclohexyl triisocyanate is formed in situ from the corresponding tricarboxylic acid azide by means of an Curtius rearrangement (C. F. H. Allen, A. Bell, *Organic Synthesis Collective Volume* 3, 6 ed (1967) 846-847 and subsequently reacted with a free amino group of an an acid derivative, such as an amino acid alkyl ester or amide or an amino acid glycol ester or amide.

In another embodiment the free amino group of an amino acid derivative is activated at first (in situ formation of the isocyanate, H. J. Knolker, T. Braxmeier, *Synlett.* (1997) 925-928 and subsequently reacted with triaminocyclohexane.

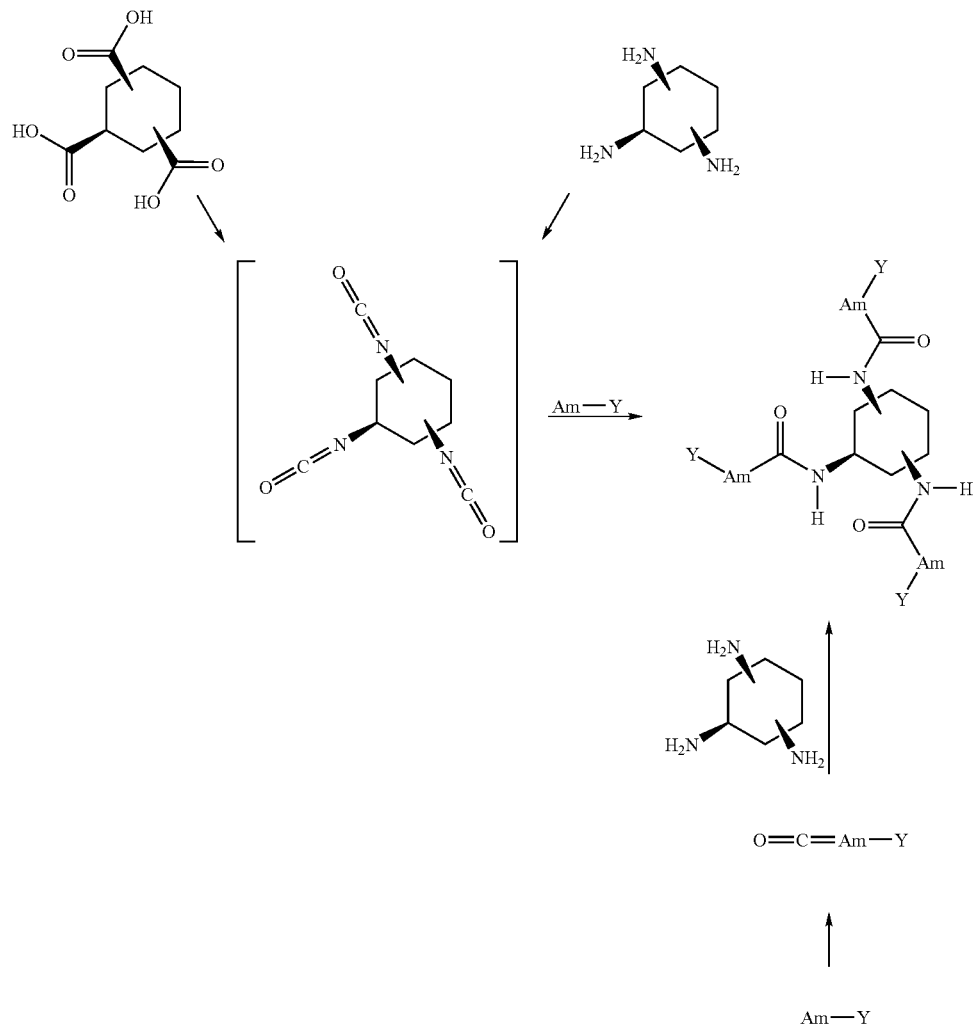

Group 6

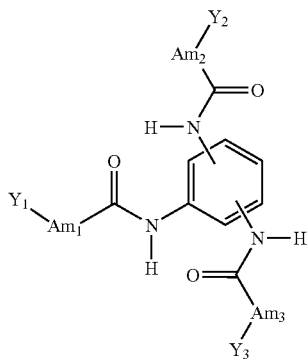

A thickener or gelling agent according to this formula can be prepared by reaction of a triaminobenzene with an isocyanate (in situ formed) of an amidated/esterified amino acid ((H-J Knolker, T. Braxmeier, *Synlett*. (1997) 925-928) or (in situ) formation of the triisocyanate (C. F. H. Allen, As Bell, *Organic Synthesis Collective Volume* 3, 6 ed. (1967) 846-847, J. E. Gill, R. MacGillivray. J. Munro, *J. Chem. Soc.* (1949) 1753-1754) and subsequent reaction with three equivalents of the free amino group of an amino acid derivative, such as an aminoacid alkyl ester or amide or an aminoacid glycol ester or amide (see compounds 5).

Typically, the amino acid based compounds described herein were found to be able to thicken or get numerous solvents, including aromatic, non-aromatic hydrocarbons, alcohols, ethers, esters, aldehydes, ketones, alkanoic acids, epoxides, amines, halogenated hydrocarbons, silicon ails, vegetable oils, phosphoric acids, sulfoxides, water and mixtures thereof. By using the appropriate compounds or mixtures thereof the range of gelated or thickened solvents can be tuned and the solvents can either be gelated or thickened.

In a preferred embodiment, water or an aqueous solvent is gelated. In accordance with this embodiment, the gelling agent preferably has a 1,3,5-substituted cyclohexyl core (Z in formula (I) above). Each of $X_1$, $X_2$, and $X_3$ is preferably —C(O)—. Each of $Am_1$, $Am_2$, and $Am_3$ is preferably the same and chosen from the group of α, β and γ-amino acids, of which both the d and the l isomers are eligible. Particularly preferred are α-amino acids, in which the carbon atom a to the —COOH terminus is substituted with a hydrophobic group. Examples of these preferred α-amino acids are phenyl alanine, methionine, histidine, isoleucine, leucine, tryptophan, tyrosine, and valine. Each of $Y_1$, $Y_2$, and $Y_3$ is preferably the same and chosen from the group of —OH, —OCH$_3$, —OCH$_2$CH$_3$, —OCH$_2$CH$_2$OH, —NH$_3$, —NHCH$_2$CH$_2$CH$_2$CH$_2$OH, —OCH$_2$CH$_2$OCH$_2$CH$_3$, —OCH$_2$CH$_2$OCH$_2$CH$_2$OH, —NHOH, —NHCH$_3$, —NH—CH$_2$-p-C$_6$H$_4$—B(OH)$_2$, or —NHCH$_2$CH$_2$OH.

To obtain a gel or to thicken the solvent, the compound is mixed with the required solvent or a mixture of solvents in an amount between 0.01 and 50 wt. %, based on the weight of the composition. Typically, the mixing of the components will be performed by heating (in some cases it may be helpful to homogenize the components, e.g. vortex) them together at temperatures of 20-200° C., preferably 60-150° C. Cooling these hot mixtures to a preferred temperature in the range of −20 to 100° C., preferably 4 to 100° C. affords the gel or thickened solvent. The obtained gels have been found to comprise thin, intertwining fibers. In an alternative embodiment, the gelling agent is first dissolved in a polar or apolar solvent and then added or sprayed into a composition or solvent to be converted into a gel. Of course, it is also possible to add or spray a composition or solvent to be converted into a gel into a solution of the gelling agent in a polar or apolar solvent.

Alternatively, some other methods to produce gels are dependent on an environmental stimulus, such as light, pH and/or chemical stimuli. Photo-controlled gelation and pH controlled gelation are two mechanisms which can be used to induce the sol to gel transition, while in some case this process is reversible and thus can also be used for gel to sol transition. Chemical inducers for triggering gel-to-sol or sol-to-gel formation are disulfide reducing enzymes and thiol oxidizing enzymes, which in nature also occur in the human body. Also tris-(2-carboxy ethyl)phosphine, mercaptoethanol, 1,4-dithiothreitol, glutathione and dimethyl sulfoxide (DMSO) can be used for chemical triggering. One further way to form a gel is by mixing solutions of two different gelling agents, which each independently at the reaction temperature and concentration remains in the sol phase, but when mixed transit to the gel phase.

The obtained gels can be used as a chromatographic support for chiral recognition or for covalent binding of a catalyst. They can furthermore be used as drug delivery vehicle, e.g. as disclosed in international patent application PCT/NL03/00256. In accordance with this embodiment, the gels can be used as the vehicle in delivery vehicles for delivering a substance of interest, in particular a drug, to a predetermined site in vivo, said vehicle comprising said substance and a means for inducing availability of at least one compartment of said vehicle toward the exterior, thereby allowing access of said substance to the exterior of said vehicle at said predetermined site. Preferably, the substance to be made available in an induced way at the predetermined site, is incorporated in the gel at the time of gel formation. However, this need not always be true. Substances may also be allowed to enter a preformed gel under the appropriate conditions.

Surprisingly, it has been found that formation of gels comprising a drug for controlled delivery can be used to produce very small particles of the drug, which have been found to be impossible to produce in conventional manners such as milling. This is particularly important for (oral) administration of drugs which are not or difficult to dissolve in water or aqueous systems. To achieve the small particle size, the drug may be dissolved in an organic solvent, such as dimethylsulfoxide (DMSO) or ethanol, together with a gelling agent or thickener according to the invention. Upon addition of water, gel formation occurs. The water insoluble drug also precipitates in the form of very small particles (<70 nm). If desired, the DMSO or ethanol can be washed out of the system, leaving au aqueous gel contain the small drug particles. These may be lyophilized and formulated into a pharmaceutical product. It is also possible to wash out the gelling agent or thickener, leaving only the small drug particles for use in the formulation of a pharmaceutical product.

The invention will now be further illustrated by the following, non-restrictive examples.

EXAMPLES

Synthesis of 1,3,5-Benzenetricarbonyl Trichloride (MdL012)

1,3,5-benzenetricarboxylic acid (6.0 g, 28.7 mmol) was placed in a flask together with SOCl$_2$ (12 ml) and a drop of DMF. The suspension was refluxed for 3 h, resulting in a clear solution. The remaining SOCl$_2$ was evaporated in vacuo, yielding a pale yellow oil which formed crystals upon standing in the cooling cell (7.7 g, 28.7 mmol 100%).

Synthesis of cis, cis-1,3,5-Cyclohexanetricarbonyl Trichloride (MdL044)

cis, cis-1,3,5-cyclohexane tricarboxylic acid (3.0 g, 13.9 mmol) was placed in a flask together with $SOCl_2$ (8 ml). The suspension was refluxed for h, resulting in a clear solution. The remaining $SOCl_2$ was evaporated in vacuo, yielding a pale yellow oil which formed crystals upon standing in the cooling cell (3.77 g, 13.9 mmol, 100%).

Synthesis of L-Phenylalanine Actyl Ester (MdL063)

L-Phenylalanine (5.0 g, 0.03 mol), 1-octanol (3.9 g, 0.03 mol) and p-toluenesulfonic acid monohydrate (6.3 g, 0.038 mol) were suspended in toluene (200 ml) in a flask equipped with a Dean-Stark trap and refluxed for 20 h., resulting in a clear solution. Subsequently, the solvent was removed in vacuo and the remaining white solid was dissolved in $CHCl_3$ (150 ml). This solution was extracted with 10% sodium carbonate, water and brine and dried over $MgSO_4$. Evaporation of the solvent in vacuo yielded a colourless oil (7.7 g, 0.028 mol, 92%). $^1H$ NMR ($CDCl_3$): δ=7.19 (m, 5H), 4.04 (t, 2H, $^3J$=6.59 Hz), 3.67 (dd, 1H, $^3J_{AB}$=5.5 Hz, $^3J_{AB}$=7.7 Hz), 3.03 (dd, 1H, $^2J_{AB}$=13.6 Hz, $^3J_{AB}$=5.5 Hz), 2.81 (dd, 1H, $^2J_{AB}$=13.6 Hz, $^3J_{AB}$=7.7 Hz), 1.54 (m, 2H), 1.47 (s, 2H), 1.22 (a, 10H), 0.83 (t, 3H, $^3J$=6.8 Hz); $^{13}C$ NMR ($CDCl_3$): δ=175.1, 137.15, 129.15, 128.40, 126.65, 65.02, 55.75, 41.06, 31.65, 29.06, 28.41, 25.74, 22.51, 13.97.

Synthesis of L-Leucine Octyl Ester (MdL060)

L-Leucine (5.0 g, 0.038 mol), 1-octanol (5.0 g, 0.038 mol) and p-toluenesulfonic acid monohydrate (8.0 g, 0.042 mol) were suspended in toluene (200 ml) in a flask equipped with a Dean-Stark trap and refluxed for 20 h. Subsequently, the solvent was removed in vacuo and the remaining white solid was dissolved in $CHCl_3$ (150 ml). This solution was extracted with 10%1/sodium carbonate, water and brine and dried Over $MgSO_4$, Evaporation of the solvent in vacuo yielded a colourless oil (9.0 g, 0.037 mol, 97%). $^1H$ NMR ($CDCl_3$): δ=4.18 (t, 2H, $^3J$=7.0 Hz), 3.63 (dd, 1H, $^3J_{AB}$=8.4 Hz, $^3J_{AB}$=5.9 Hz), 1.85 (m, 1H), 1.74-3.18 (m, 6H), 1.37 (s, 10H, 0.99 (t's, 9H); $^{13}C$ NMR ($CDCl_3$): δ=176.98, 64.82, 52.79, 44.06, 31.64, 29.04, 28.47, 25.76, 24.66, 22.81, 22.51, 21.77, 13.96

Synthesis of Glycine octyl ester (MdL105)/octyl 2-aminoacetate

Glycine (2.86 g, 0.038 mol), 1-octanol (6.0 g, 0.038 mol) and p-toluenesulfonic acid monohydrate (8.0 g, 0.042 mol) were suspended in toluene (200 ml) in a flask equipped with a Dean-Stark trap and refluxed for 20 h. Subsequently, the solvent was removed in vacuo and the remaining white solid was dissolved in $CHCl_3$ (160 ml). This solution was extracted with 10% sodium carbonate (3×100 ml), water (3×80 ml) and brine and dried over $MgSO_4$. Evaporation of the solvent in vacuo yielded MdL105 as a colourless oil (6.75 g, 0.036 mol, 95%). $^1H$ NMR ($CDCl_3$): δ=4.11 (t, 2H, $^3J$=6.8 Hz), 3.41 (s, 2H), 1.61 (m, 2H), 1.49 (s, 2H), 1.28 (m, 10H), 0.87 (t, 3H, $^3J$=6.6 Hz); $^{13}C$ NMR ($CDCl_3$): δ=174.24, 64.91, 43.82, 31.61, 29.03, 28.45, 25.71, 22.47, 13.92.

Synthesis of L-phenylalanine 9-decen-1-ol ester (MdL058)

L-Phenylalanine (5.0, 0.03 mol), 9-decen-1-ol (4.69 g, 0.03 mol) and p-toluenesulfonic acid monohydrate (6.3 g, 0.033 mol) were suspended in toluene (200 ml) in a flask equipped with a Dean-Stark trap and refluxed for 20 h. Subsequently, the solvent was removed in vacuo and the remaining white solid was dissolved in $CHCl_3$ (150 ml). This solution was extracted with 10% sodium carbonate, water and brine and dried over $MgSO_4$. Evaporation of the solvent in vacuo yielded a colourless oil (8.11 g, 0.027 mol, 89%). $^1H$ NMR ($CDCl_3$): δ=7.20 (m, 5H), 6.76 (m, 1H), 4.92 (m, 2H), 4.04 (t, 2H, $^3J$=6.8 Hz), 3.67 (dd, 1H, $^3J_{AB}$=5.5 Hz, $^3J_{AB}$=7.7 Hz), 3.02 (dd, 1H, $^2J_{AB}$=13.6 Hz, $^3J_{AB}$=5.5 Hz), 2.81 (dd, 1H, $^2J_{AB}$=13.6 Hz, $^3J_{AB}$=7.7 Hz), 1.99 (m, 2H), 1.51 (a, 4H), 1.24 (m, 10H); $^{13}C$ NMR($CDCl_3$): δ=169.47, 139.02, 137.16, 129.16, 128.41, 126.68, 114.07, 65.01, 55.76, 41.07, 33.65, 29.20, 29.05, 28.91, 28.75, 28.42, 25.73.

Synthesis of BOC-L-Phenylalanine octyl amide (MdL080)

To a solution of 1-octylamine (0.9 g, 6.9 mmol) and triethylamine (0.7 g, 6.9 mmol) in ethyl acetate (80 ml) was added a solution of BOC-Phe-OSu (2.5 g, 6.9 mmol) in ethyl acetate (50 ml). The mixture was stirred at room temperature for 20 hours. The organic layer was washed with water, 10% sodium carbonate, water and brine and denied on $MgSO_4$. Evaporation of the solvent in vacuo yielded MdL080 as a white powder (2.5 g, 6.6 mmol, 96%). $^1H$ NMR ($CDCl_3$): δ=7.26-7.14 (m, 5H), 5.59 (bp 1H), 5.02 (bp, 1H), 4.20 (m, 1H), 3.07 (m, 4H), 1.57-1.17 (m, 21H), 0.82 (t, 3H, $^3J$=6.8 Hz); $^{13}C$ NMR ($CDCl_3$): δ=170.98, 136.68, 129.19, 128.60, 126.76, 65.88, 39.34, 88.71, 31.66, 29.21, 29.07, 28.16, 26.64, 22.52, 13.97.

Synthesis of L-Phenylalanine octyl amide (MdL82)

MdL080 (2.0 g, 5.3 mmol) was added to a solution of TFA (22.8 g, 0.2 mmol) in $CH_2Cl_2$ (100 ml) and stirred for 2 hours. After reaction, the solution was extracted with water, 1N aqueous NaOH and brine and dried over $MgSO_4$. Evaporation in vacuo of the solvent and TFA yielded MdL080 as a white powder (1.2 g, 4.3 mmol, 81%). $^1H$ NMR ($CDCl_3$): δ=7.28-7.15 (m, 6H), 3.53 (m, 1H), 3.18 (m, 3H), 2.63 (m, 1H), 2.67-2.59 (m, 14H), 0.82 (t, 3H, $^3J$=6.4 Hz); $^{13}C$ NMR ($CDCl_3$): δ=173.88, 137.91, 129.19, 128.56, 126.65, 56.36, 40.97, 38.98, 31.68, 29.46, 29.15, 29.09, 26.82, 22.53, 18.99.

Synthesis of Z-Glycine octyl amide (MdL078)

To a solution of 1-octylamine (1.1 g, 8.2 mmol) and triethylamine (0.8 g, 8.2 mmol) in ethyl acetate (80 ml) was added a solution of Z-Gly-OSu (2.5 g, 8.2 mmol) in ethyl acetate (100 ml). The mixture was stirred at room temperature for 70 hours. Water was added and the organic layer was separated and washed with water, 10% sodium carbonate, water and brine and dried on $MgSO_4$. Evaporation of the solvent in vacuo yielded MdL078 as a white solid (2.3 g, 7.2 mmol, 86%). $^1H$ NMR ($CDCl_3$): δ=7.36 (bp, 5H), 5.96 (bp, 1H), 5.42 (s, 1H), 5.13 (s, 2H), 3.84 (d, 2H, $^3J$=5.9 Hz), 3.26 (m, 2H), 1.48 (s, 2H), 1.27 (s, 10H), 0.88 (t, 5H, $^3J$=6.4 Hz); $^{13}C$ NMR ($CDCl_3$): δ=170.33, 156.46, 139.27, 128.46, 128.19, 128.0, 67.12, 44.58, 39.49, 31.66, 29.36, 31.06, 26.73, 22.52, 18.97.

Synthesis of Glycine octyl amide (MdL079)

The protected glycine octyl amide MdL078 (2.2 g, 6.9 mmol) was dissolved in methanol (200 ml) and a spatula Pd/C (5%) was added. The mixture was first placed under a nitrogen atmosphere and subsequently under a hydrogen atmosphere hydrogen balloon). After stirring at room temperature for 120 hours, the hydrogen gas was removed by a nitrogen flow and the Pd/C was filtered of over Celite. The solvent was evaporated in vacuo yielding MdL079 as an oil, that formed crystals upon cooling (1.8 g, 6.9 mmol, 100%). $^1$H NMR (CDCl$_3$): δ=0.26 (bp 1H), 3.35 (s, 2H), 3.26 (m, 2H), 1.67 (s, 2H), 1.51 (m, 2H), 1.26 (s, 10H), 0.87 (t, 3H, $^3$J=6.4 Hz); $^{13}$C NMR (CDCl$_3$): δ=172.25, 44.55, 38.89, 31.67, 29.52, 29.16, 29.09, 26.86, 22.52, 13.98.

Synthesis of Benz-U-Phe (MdL038)

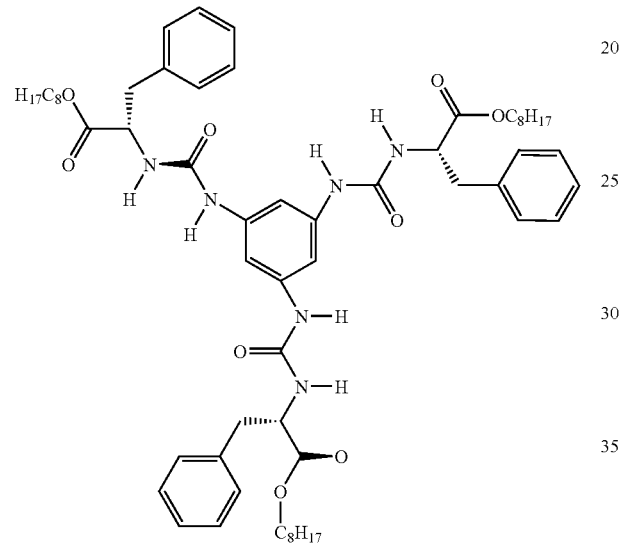

To a cooled (0° C.) solution of NaN$_3$ (1.75 g, 0.027 mol) in H$_2$O (10 ml) was added a cooled (0° C.) solution of 1,3,5-benzenetricarbonyl trichloride MdL012 (1.0 g, 3.77 mmol) in THF (10 ml). The mixture was stirred for 2 hours at 0° C. resulting in the formation of 1,3,5-benzenetricarbonyl triazide as a white precipitate. This precipitate can easily be isolated by filtration, however, because of the explosiveness of the dry solid this is strongly discouraged. Thus, cold toluene (100 ml) was added to the mixture to take up the acyl azide. The toluene layer was separated and washed with H$_2$O and brine and dried over MgSO$_4$. Subsequently, the toluene solution was heated at 100° C. till gas evolution stopped, yielding in situ the corresponding triisocyanate. The solution was allowed to cool to room temperature and MdL063 (3.45 g, 12.44 mmol) in toluene (30 ml) was added. The mixture was stirred for one night at room temperature, after which the solvents were evaporated in vacuo yielding a sticky solid. Column chromatography using an eluent gradient (CH$_2$Cl$_2$/MeOH; 200/0→200/5) on silica gel yielded MdL038 slightly contaminated. A second column chromatography (CH$_2$Cl$_3$/MeOH; 200/10) on silica gel yielded MdL038 as a pure colorless sticky solid (0.76 g, 0.74 mmol, 20%). $^1$H NMR (DMSO-d6): δ=8.62 (s, 3H), 7.31-7.16 (m, 15H), 7.08 (s, 3H), 6.27 (d, 3H, $^3$J=7.7 Hz), 4.44 (m, 3H), 3.99 (t, 6H, $^3$J=6.4 Hz), 2.97 (m, 6H), 1.48 (s, 6H), 1.20 (s, 30H), 0.83 (t, 9H, $^3$J=6.6 Hz); $^{13}$C NMR (DMSO-d6): δ=172.40, 164.66, 140.65, 136.93, 129.34, 128.65, 126.89, 100.55, 64.76, 54.04, 37.66, 31.41, 28.79, 28.20, 25.50, 22.26, 14.13; C$_{60}$H$_{84}$N$_6$O$_9$: calcd. C, 69.14; H, 8.19; N, 8.13. found: C, 69.72; H, 8.23; N, 8.12.

Gelates/thickens: hexadecane, cyclohexane, hexane, olive oil.

Synthesis of Benz-U-Leu (MdL015)

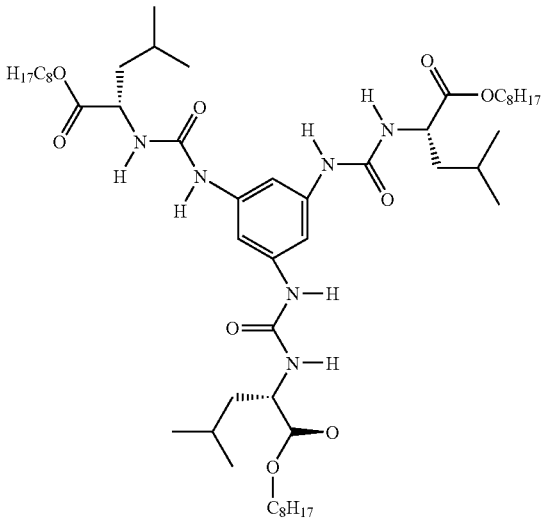

MdL015 was synthesized following the same procedure as described for MdL038, using NaN$_3$ (1.75 g, 0.027 mol), MdL012 (1.0 g, 3.77 mmol) and MdL060 (2.75 g, 11.3 mmol). After reaction an orange sticky solid was obtained and column chromatography (CH$_2$Cl$_2$/MeOH; 200/5) on silica gel yielded MdL015 as a pure, sticky solid (1.25 g, 1.34 mmol, 36%). $^1$H NMR (DMSO-d6): δ=8.49 (s, 3H), 7.09 (s, 3H), 6.30 (d, 3H, $^3$J=7.7 Hz), 4.19 (m, 3H), 4.03 (m, 6H), 1.68-1.46 (m, 15H), 1.20 (m, 30H), 0.85 (m, 27H); $^{13}$C NMR (DMSO-d6): δ=173.30, 154.58, 140.53, 100.19, 64.34, 50.80, 40.86, 31.81, 28.58, 28.54, 28.06, 25.31, 24.34, 22.85, 22.09, 21.62, 13.91.

Gelates/thickens: hexadecane, cyclohexane.

Synthesis of Benz-Am-Phe (MdL064)

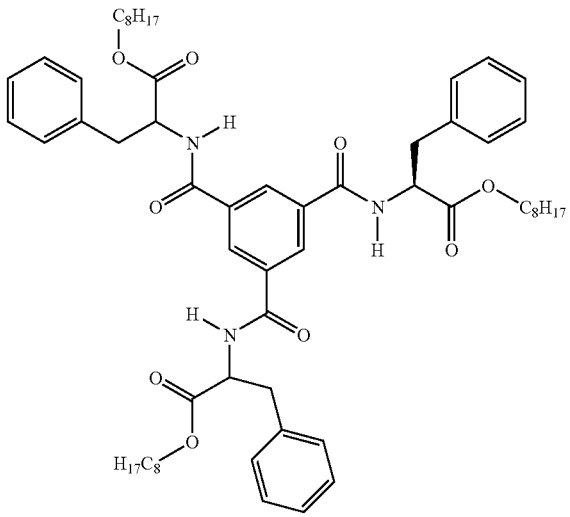

To a cooled solution of MdL068 (2.0 g, 7.2 mmol) and triethyl amine (0.73 g, 7.2 mmol) in dry CH$_2$Cl$_2$ (50 ml) was added a solution of 1,3,5-benzenetricarbonyl trichloride MdL012 (0.64 g, 2.4 mmol) in dry CH$_2$Cl$_2$ (5 ml). The solution was slowly brought to room temperature and stirred for 20 h. Subsequently CHCl$_3$ (20 ml) was added and the solution was extracted successively with dilute HCl, water, 10% sodium carbonate, water, brine. The solution was dried over MgSO$_4$ and the solvents were evaporated in vacuo, yielding a sticky solid. Column chromatography (CH$_2$Cl$_2$/MeOH; 100/1) on silica gel yielded MdL064 (1.2 g, 1.21 mmol, 50%) as a white sticky solid. $^1$H NMR (DMSO-d6): δ=9.12 (d, 3H, $^3$J=7.3 Hz), 8.39 (s, 3H), 7.26 (m, 15H), 4.67 (m, 3H), 4.01 (t, 6H, $^3$J=6.4 Hz), 3.13 (d, 6H, $^3$J=8.4 Hz), 1.48 (s, 6H), 1.17 (s, 30H), 0.80 (t, 9H, $^3$J=6.6 Hz); $^{13}$C NMR (DMSO-d6): δ=171.55, 165.54, 137.58, 134.16, 129.29, 129.02, 128.26, 126.49, 64.57, 54.62, 36.32, 21.19, 28.58, 28.04, 25.28, 22.07, 13.92; C$_{66}$H$_{31}$N$_3$O$_9$: calcd. C, 72.92; H, 8.26; N, 4.25. found: C, 72.83; H, 8.33; N, 4.25.

Gelates/thickens: cyclohexane, hexane, olive oil.

Synthesis of CHex-Am-Phe (MdL045)

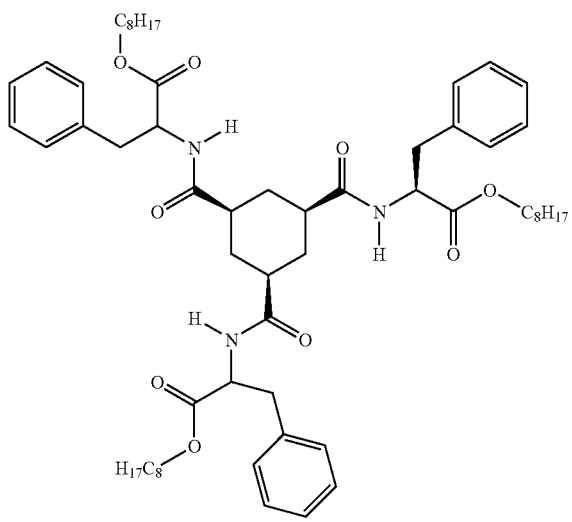

To a cooled solution of MdL063 (1.0 g, 3.6 mmol) and triethyl amine (0.36 g, 3.6 mmol) in dry CH$_2$Cl$_2$ (20 ml) was added a solution of cis-1,3,5-cyclohexane tricarbonyl trichloride MdL044 (0.33 g, 1.2 mmol) in dry CH$_2$Cl$_2$ (5 ml). The solution was slowly brought to room temperature and stirred for 20 h. Subsequently, the solution was extracted with dilute HCl, water, 10% sodium carbonate, water and brine. The solution was dried over MgSO$_4$ and the solvent was evaporated in vacuo, yielding a sticky solid. Column chromatography (CH$_2$Cl$_2$/MeOH; 100/5) on silica gel yielded MdL045 (0.3 g, 0.3 mmol, 25%) as a white sticky solid. $^1$H NMR (CDCl$_3$): δ=7.24-7.01 (m, 15H), 5.85 (d, 5H, $^3$J=7.7 Hz), 4.82 (m, 3H), 4.06 (m, 6H, 3.06 (m, 6H), 2.09 (t, 5H, $^3$J=12 Hz), 1.91 (d, 3H, $^3$J=12 Hz), 1.54 (s, 9H), 1.23 (s, 80H), 0.83 (t, 9H, $^3$J=6.6 Hz); $^{13}$C NMR (DMSO-d6): δ=174.16, 171.70, 187.30, 128.98, 128.12, 126.44, 64.37, 53.40, 42.09, 36.64, 31.20, 28.53, 27.98, 25.19, 22.06, 13.93.

Gelates/thickens: hexadecane, cyclohexane, hexane, p-xylene, tetraline, BuOAc, cyclohexanone, olive oil, dichloroethane, 1-octanol, ethanol.

Synthesis of CHex-Am-Leu (MdL061)

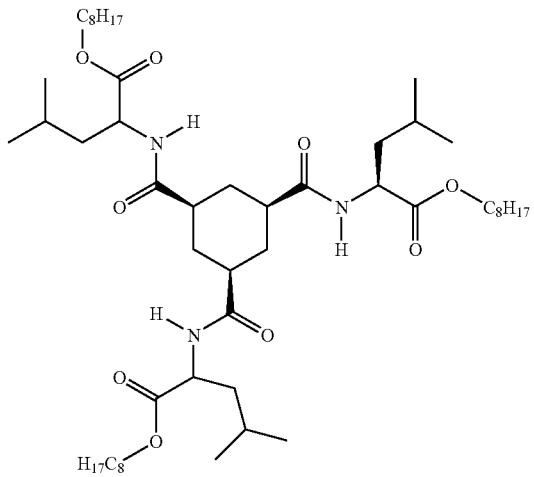

MdL061 was synthesized following the same procedure as described for MdL045, using MdL060 (2.0 g, 8.2 mmol), triethyl amine (0.83 g, 8.2 mmol) and cis,cis-1,3,5-cyclohexane tricarbonyl trichloride MdL044 (0.74 g, 2.73 mmol). Column chromatography using an eluent gradient (CH$_2$Cl$_2$/MeOH; 200/5→200/10) on silica gel yielded MdL061 (1.06 g, 1.19 mmol, 44%) as a white sticky solid. $^1$H NMR (DMSO-d6): δ=8.11 (d, 5H, $^3$J=7.7 Hz), 4.22 (m, 3H), 3.99 (m, 6H), 2.27 (t, 3H, $^3$J=12.1 Hz), 1.69-1.35 (m, 21H), 1.23 (s, 30H), 0.84 (m, 27H); $^{13}$C NMR (DMSO-d6): δ=174.37, 172.69, 64.27, 50.17, 42.31, 31.19, 28.58, 28.50, 28.04, 25.24, 24.35, 22.73, 22.08, 21.21, 18.97.

Gelates/thickens: hexadecane, cyclohexane, hexane, p-xylene, BuOAc, olive oil.

Synthesis of CHex-Am-Phe-decene (MdL059)

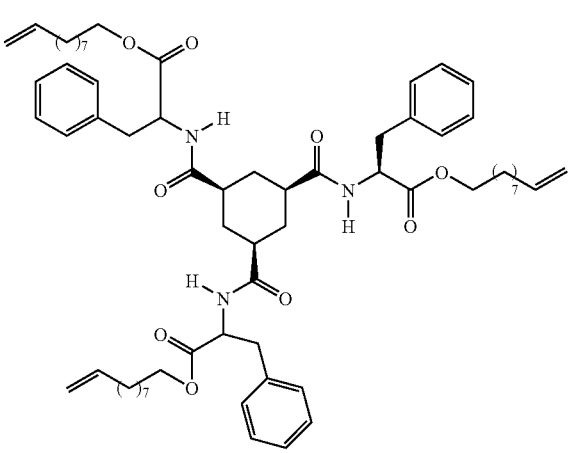

MdL059 was synthesized following the same procedure as described for MdL045, using MdL058 (2.0 g, 6.6 mmol) and triethyl amine (0.67 g, 6.6 mmol) in dry $CH_2Cl_2$ (50 ml) and cis,cis-1,3,5-cyclohexane tricarbonyl trichloride MdL044 (0.6 g, 2.2 mmol). Column chromatography ($CH_2Cl_2$/MeOH; 100/5) on silica gel yielded MdL059 (1.8 g, 1.7 mmol, 77%) as an opaque sticky solid. $^1$H NMR (DMSO-d6): δ=8.19 (d, 3H, $^3J$=7.7 Hz), 7.21 (m, 15H), 5.77 (m, 3H), 4.95 (m, 6H), 4.39 (m, 3H), 3.96 (t, 6H, $^3J$=6.2 Hz), 2.92 (m, 6H), 2.17 (t, 3H, $^3J$=12.6 Hz), 1.98 (m, 6H), 1.45 (m, 9H), 1.20 (m, 33H); $^{13}$C NMR (DMSO-d6): δ=174.16, 171.71, 138.81, 137.29, 128.98, 128.13, 126.44, 114.60, 64.39, 53.40, 42.10, 36.64, 33.20, 31.02, 28.70, 28.54, 28.46, 28.24, 27.98, 25.20.

Gelates/thickens: hexadecane, cyclohexane, hexane, p-xylene, tetraline, BuOAc, olive oil, 1-octanol.

Synthesis of CHex-U-Phe (MdL066)

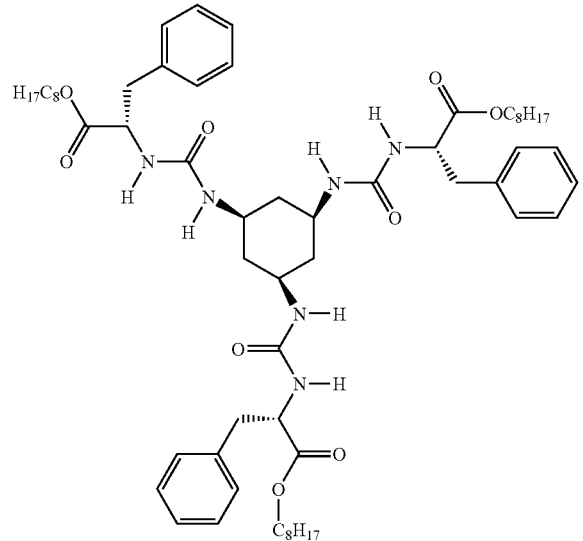

To a solution of di-tert-butyl dicarbonate (0.88 g, 3.8 mmol) and 4-dimethylamino pyridine (44 mg, 0.36 mmol; added in dry $CH_2Cl_2$ (3 ml)) in dry $CH_2Cl_2$ (10 ml) was added a solution of MdL063 (1.0 g, 3.6 mmol) in dry $CH_2Cl_2$ (6 ml). The mixture was stirred for 30 minutes at room temperature till gas evolution stopped and subsequently cis, cis-1,3,5-triaminocyclohexane (0.14 g, 1.1 mmol) in $CH_2Cl_2$ (5 ml) was added. The obtained turbid mixture was first stirred at room temperature for 30 minutes and then at 40° C. for 48 hours. After cooling, the solvent was evaporated in vacuo. The residue was refluxed in ethanol and filtered off, yielding MdL066 as a white powder (0.5 g, 3.87 mmol, 85%). $^1$H NMR (DMSO-d6): δ=7.28-7.13 (m, 15H), 6803 (m, 6H), 4.36 (m, 30, 3.96 (m, 6H), 3.35 (m, 6H), 2.91 (m, 6H), 1.83 (bd, 3H, $^3J$=8.8 Hz), 1.46 (m, 6H), 1.22 (s, 30H), 0.84 (t, 9H, $^3J$=6.4 Hz).

Gelates/thickens: p-xylene, tetraline, BuOAc, cyclohexanone, dichloroethane, 1-octanol.

Synthesis of CHex-Am-PheAm (MdL083)

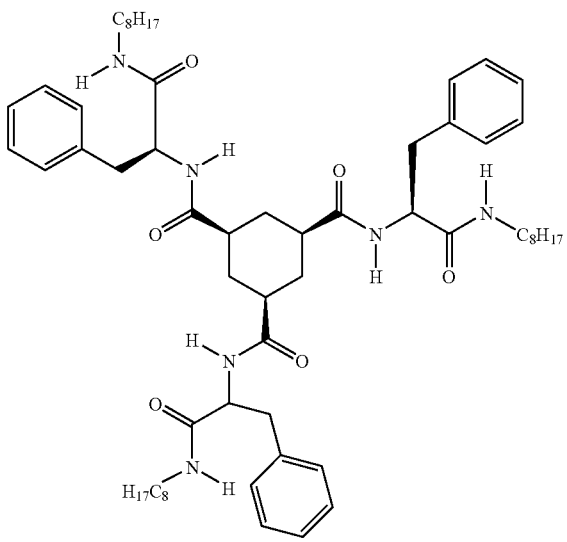

To a cooled solution of MdL082 (1.0, 3.6 mmol) and triethyl are (0.36 g, 3.6 mmol) in dry $CH_2Cl_2$ (50 ml) was added a solution of cis,cis-1,3,5-cyclohexane tricarbonyl trichloride MdL044 (0.33 g, 1.2 mmol) in dry $CH_2Cl_2$ (5 ml). A viscous, turbid mixture was formed, which was slowly brought to room temperature and stirred for 20 h. The solvent was evaporated in vacuo, yielding a white solid. Stirring in ethanol to remove the HCl-salts followed by filtration afforded MdL083 as a white powder (1.1 g, 1.11 mmol, 92%) $^1$H NMR ($CDCl_3$+TFA): δ=7.68 (d, 3H, $^3J$=8.4 Hz), 7.24-7.05 (m, 15H), 6.69 (s, 3H), 4.69 (m, 3H), 3.14 (m, 3H), 3.00-2.90 (m, 9H), 2.31 (t, 3H, $^3J$=11.5 Hz), 1.78 (d, 3H, $^2J_{AB}$=12.5 Hz), 1.45 (dt, 3H, $^2J_{AB}$=12.5 Hz, $^3J_{AB}$=11.5 Hz), 1.22-1.02 (m, 36H), 0.82 (t, 9H, $^3J$=6.8 Hz); $^{13}$C NMR ($CDCl_3$+TFA): δ=176.64, 172.17, 134.43, 128.92, 128.89, 127.69, 55.78, 42.59, 40.68, 38.20, 31.65, 30.12, 28.93, 28.89, 28.21, 26.39, 22.50, 13.83.

Gelates/thickens: p-xylene, tetraline, cyclohexanone, dichloroethane.

Synthesis of CHex-Am-GlyAm (MdL081)

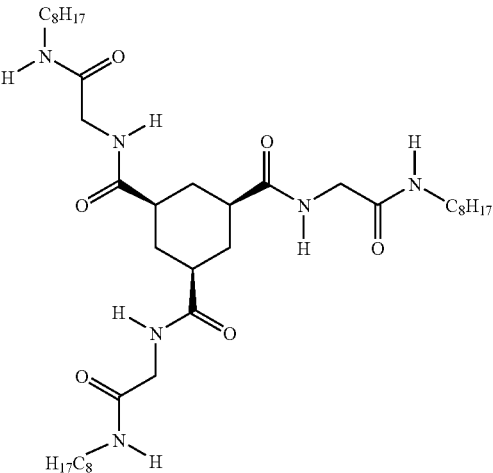

MdL081 was synthesized following the same procedure as described for MdL083, using MdL079 (1.0 g, 5.87 mmol), triethyl amine (0.54 g, 5.37 mmol) and cis,cis-1,3,5-cyclohexane tricarbonyl trichloride MdL044 (0.49 g, 1.8 mmol). The solvent was evaporated in vacuo, yielding a white, waxy solid. Stirring in ethanol to remove the HCl-salts followed by filtration afforded MdL081 as a white powder (0.94 g, 1.3 mmol, 72%). $^1$H NMR (DMSO-d6, 80° C.) δ=7.65 (bt, 3H, $^3$J=5.5 Hz), 7.46 (bs, 3H), 3.64 (d, 6H, $^3$J=5.5 Hz), 3.04 (m, 6H), 2.29 (bt, 5H, $^3$J=12.1 Hz), 1.88 (bd, 3H, $^2$J=12.5 Hz), 1.48-1.19 (m, 39H), 0.86 (t, 9H, $^3$J=6.4 Hz).

Gelates/thickens: p-xylene, tetraline, BuOAc, cyclohexanone, 1-octanol, ethanol.

Synthesis of CHex-Am-Gly (MdL106)

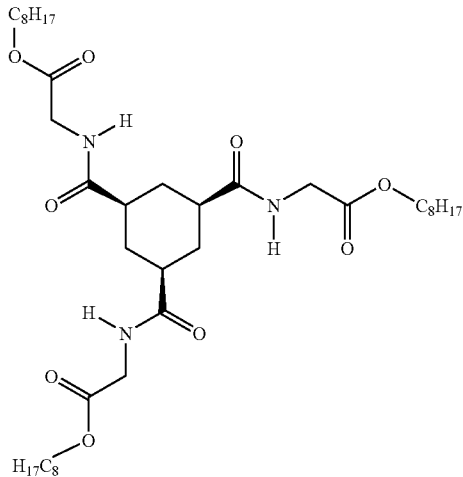

MdL106 was synthesized following the same procedure as described for MdL045, using MdL105 (1.53 g, 8.2 mmol), triethyl amine (0.83 g, 8.2 mmol) and cis,cis-1,3,5-cyclohexane tricarbonyl trichloride MdL044 (0.74 g, 2.73 mmol). After drying of the solution over MgSO$_4$ and evaporation of the solvent in vacuo, MdL106 was obtained as an analytical pure, white solid (1.67 g, 2.4 mmol, 88%). $^1$H NMR (DMSO-d6): δ=8.21 (t, 3H, $^3$J=5.7 Hz), 4.00 (t, 6H, $^3$J=6.6 Hz), 3.77 (d, 6H, $^3$J=5.8 Hz), 2.27 (t, 3H, $^3$J=12.3 Hz), 1.77 (bd, 3H, $^3$J=12.8 Hz), 1.53-1.24 (m, 39H), 0.84 (t, 9H, $^3$J=6.6 Hz); $^{13}$C NMR (DMSO-d6): δ=174.68, 169.94, 64.28, 42.24, 40.56, 31.22, 28.59, 28.09, 25.29, 22.07, 13.95.

Gelates/thickens: cycloheane, p-xylene, tetraline, BuOAc, cyclohexanone, olive oil, 1-octanol, ethanol.

Synthesis of CHex-U-Leu (MdL103)

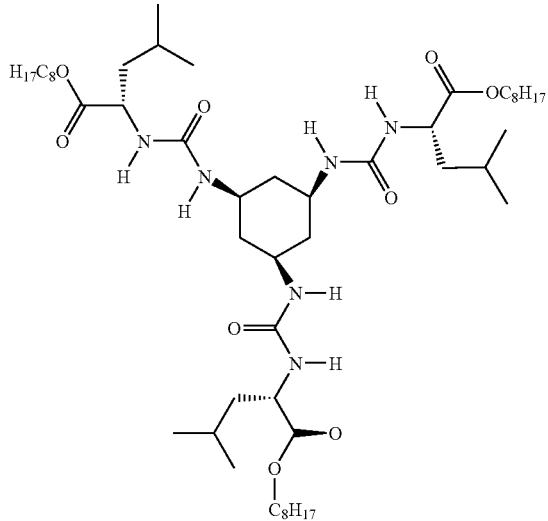

MdL103 was synthesized following the same procedure as described for MdL066, using di-tert-butyl dicarbonate (1.66 g, 7.6 mmol) in dry CH$_2$Cl$_2$ (10 ml), 4-dimethylamino pyridine (88 mg, 0.72 mmol) in dry CH$_2$Cl$_2$ (6 ml), MdL060 (1.75 g, 7.2 mmol) in dry CH$_2$Cl$_2$ (12 ml) and cis, cis-1,3,5-triaminocyclohexane (0.284 g, 2.2 mmol) in CH$_2$Cl$_2$ (10 ml), yielding MdL103 as a white solid (0.94 g, 1.00 mmol 45%). $^1$H NMR (CDCl$_3$+TFA): δ=4.46 (m, 3H), 4.20 (t, 6H, $^3$J=6.6 Hz), 3.68 (m, 3H), 2.26 (bd, 3H, $^3$J=11.0 Hz), 1.63 (m, 15H), 1.27 (m, 33H), 0.90 (m, 27H); $^{13}$C NMR (CDCl$_3$+TFA): δ=175.84, 158.18, 67.51, 52.73, 46.565, 40.79, 37.41, 31.62, 28.98, 28.93, 28.04, 25.52, 24.69, 22.49, 22.20, 21.30, 18.85; decomp.>215° C.

Gelates/thickens: cyclohexane, hexane, p-xylene, BuOAc, dichloroethane, 1-octanol, ethanol.

Synthesis of Z-Leucine octyl amide (MdL084)

To a solution of 1-octylamine (1.5 g, 11.6 mmol) and triethylamine (1.11 g, 11.0 mmol) in ethyl acetate (100 ml) was added a solution of Z-Leu-OSU (4.0 g, 11.0 mmol) in ethyl acetate (80 ml). The mixture was stirred at room temperature for 70 hours. Water was added and the organic layer was separated and washed with water (1×100 ml), 10% sodium carbonate (3×100 ml), water (3×80 ml) and brine and dried on MgSO$_4$. Evaporation of the solvent in vacuo yielded MdL034 as an orange solid (4.1 g, 10.9 mmol, 99%). $^1$H NMR(CDCl$_3$): δ=7.28 (bp, 5H), 5.99 (bp, 1H), 5.18 (d, 1H, $^3$J=7.7 Hz), 5.04 (s, 2H), 4.07 (m, 1H), 3.16 (m, 2H), 1.60 (m, 2H), 1.42 (m, 3H), 1.21 (s, 10), 0.86 (m, 9H); $^{13}$C NMR (CDCl$_3$): δ=171.85, 156.18, 136.08, 128.41, 128.09, 127.88, 66.93, 53.52, 41.39, 39.44, 31.66, 29.38, 29.09, 26.72, 24.59, 22.77, 22.62, 21.97, 13.98.

Synthesis of Leucine octyl amide (MdL035)

The protected Leucine octyl amide MdL034 (3.5 g, 9.3 mmol) was dissolved in methanol (250 ml) and a spatula Pd/C (5%) was added. The mixture was first placed under a nitrogen atmosphere and subsequently under a hydrogen atmosphere (hydrogen balloon). After stirring at room temperature for 70 hours, the hydrogen gas was removed by a nitrogen flow and the Pd/C was filtered of over Celite. The solvent was evaporated in vacuo yielding MdL036 as an yellow oil, that formed crystals upon cooling (2.25 g, 9.3 mmol, 100%). $^1$H NMR (CDCl$_3$): δ=7.26 (bp, 11, 3.88 (bd, 1H, $^3$J=17.6 Hz), 3.21 (m, 2H), 2.25 (bs, 2H), 1.67 (m, 2H), 1.47 (m, M, 1.41-1.25 (m, 11H), 0.95-0.83 (m, 9H); $^{13}$C NMR (CDCl$_3$): δ=175.12, 53.84, 43.89, 38.95, 31.64, 29.44, 29.11, 29.06, 26.79, 24.73, 23.25, 22.49, 21.26, 13.94.

Synthesis of CHex-Am-LueAm (MdL086)

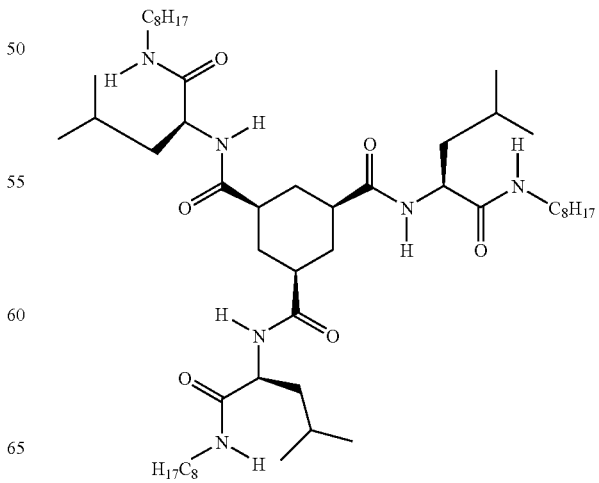

MdL086 was synthesized following the same procedure as described for MdL083, using MdL035 (0.98 g, 4.0 mmol), triethyl amine (0.36 g, 3.6 mmol) and cis,cis-1,3,5-cyclohexane tricarbonyl trichloride MdL044 (0.33 g, 1.2 mmol). The solvent was evaporated in vacuo, yielding a white, waxy solid. Stirring in ethanol to remove the HCl-salts followed by filtration afforded MdL086 as a white powder (0.62 g, 0.70 mmol 58%). $^1$H NMR (CDCl$_3$+TFA): δ=7.60 (d, 5H, $^3$J=8.1 Hz), 7.19 (s, 5H), 4.55 (m, 3H), 3.35-3.17 (m, 6H), 2.41 (t, 3H, $^3$J=11.3 Hz), 1.98 (d, 3H, $^2$J$_{AB}$=12.1 Hz), 1.69-1.51 (m, 18H), 1.26 (s, 30H, 0.89 (m, 27H); $^{13}$C NMR (CDCl$_3$+TFA): δ=176.13, 173.31, 52.41, 42.71, 40.58, 40.37, 31.58, 30.25, 28.94, 23.86, 28.38, 26.48, 24.64, 22.47, 21.97, 21.81, 13.86; decomp.>230° C.

Gelates/thickens: cyclohexane, p-xylene, tetraline, cyclohexanone, olive oil, 1-octanol.

Synthesis of Benz-Am-Phe-OMe

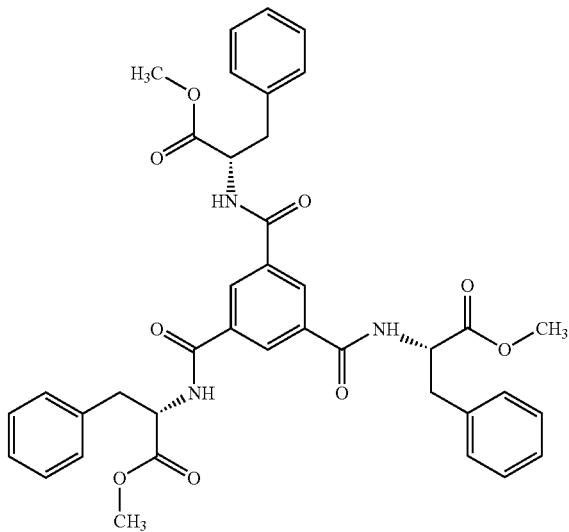

L-phenylalanine methyl ester hydrochloride (2.40 g; 11.3 mmol; 3.0 eq) in 200 ml dry CH$_2$Cl$_2$ was cooled and Et$_3$N (3.1 ml; 22.6 mmol; 6-0 eq) was added. Cis,cis-1,3,5-benzenetricarbonyl trichloride (1.00 g; 3.8 mmol; 1.0 eq) in 20 ml dry CH$_2$Cl$_2$ was added to the reaction mixture. The solution was slowly brought back to room temperature and left stirring overnight. The next morning the solvent was evaporated in vacuo and the remaining solid was recrystallized from ethanol. The crystals were collected by vacuum filtration and dried in a vacuum oven. Yield was 48% (1.25 g; 1.8 mmol). $^1$H-NMR (DMSO): δ 3.16 (m, 2H); δ 3.64 (s, 3H); δ 4.69 (s, 1H); δ 7.27 (m, Ph, 5H); δ 8.36 (s, Ph, 1H); δ 9.19 (d, $^3$J=8.1 Hz, NH, 1H). $^{18}$C-NMR (DMSO): δ 50.98, 53.40, 125.49, 127.25, 127.97, 133.12, 136.53, 164.51, 170.94. EI-MS for C$_{39}$H$_{39}$N$_3$O$_9$ calcd. 693.27. found 698 [M$^+$].

Gelates/thickens: cyclohexane, p-xylene, 2-octanol, 2-propanol.

Synthesis of Benz-Am-Met-OMe

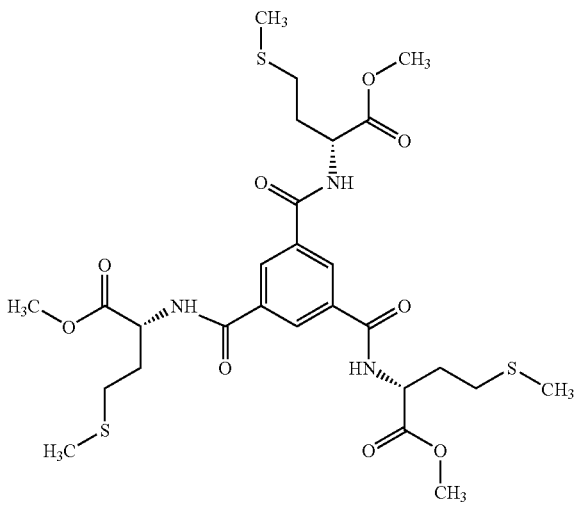

L-methionine methyl ester hydrochloride (2.30 g; 11.3 mmol; 3.0 eq) in 100 ml dry CH$_2$Cl$_2$ was cooled and Et$_3$N (3.1 ml; 22.6 mmol; 6.0 eq) was added. Cis,cis-1,3,5-benzenetricarbonyl trichloride (1.00 g; 3.8 mmol; 1.0 eq) in 20 ml dry CH$_2$Cl$_2$ was added to the reaction mixture. The solution was slowly brought back to room temperature and left stirring overnight. The next morning the solvent was evaporated in 'in vacuo' and the roar product was dissolved in 40 ml CH$_2$Cl$_2$ and 20 ml CHCl$_3$. The solution was extracted successfully with dilute HI, H$_2$O, 10% sodium carbonate, H$_2$O, brine and dried over MgSO$_4$. The solvents were evaporated 'in vacuo'. The yield was 80% (1.94 g; 3.0 mmol). $^1$H-NMR (DMSO): δ 2.07 (m, 5H, SCH$_3$+CH$_2$); δ 2.60 (m, 2H, SCH$_2$); δ 3.67 (S, 3H, OCH$_3$); δ 4.59 (q, 1H, CH); δ 8.51 (s, 1H, Ar); δ 9.13 (d, 1H, NH, $^3$J=7.3 Hz). $^{13}$C-NMR (DMSO): δ 13.48, 28.82, 28.94, 50.78, 51.03, 128.52, 183.17, 164.93, 171.28. EI-MS for C$_{27}$H$_{39}$N$_3$O$_9$S$_3$ calcd. 645.18. found 645 [M$^+$].

Gelates/thickens: toluene, n-butylacetate, 2-octanol, Z-propanol.

Synthesis of CHex-Am-Phe-OH

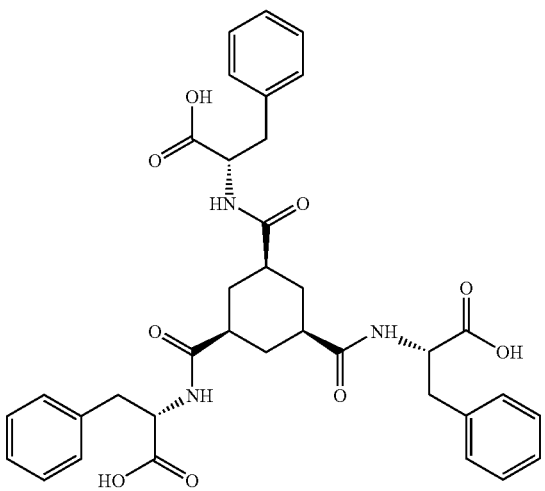

cHexAmPheOMe (0.54 g; 0.8 mmol) was added to 10 ml MeOH. The mixture was cooled and NaOH (5 ml; 2 M) was added. The e was slowly brought back to r.t. and stirred for 20 hours. The solution was diluted with water (25 ml) and 2 M HCl was added till the pH was lower than 3. A precipitate formed and was dried in the vacuum oven. The yield is 84% (0.46 g; 0.7 mmol). $^1$H-NMR (DMSO): δ 1.25 (q, 1H); δ 1.47 (d, 1H); δ 2.20 (t, 1H); δ 2.87 (t, 1H); δ 3.06 (m, 1H); 34.42 (m, 1H); δ 7.25 (s, 5H, Ph); δ 8.10 (d, $^3$J=8.3 Hz, 1H, NH). $^{13}$C-NMR (DMSO): δ 30.10, 35.63, 41.16, 52.14, 125.37, 127.09, 128.03, 136.72, 172.16, 173.11. EI-MS for $C_{36}H_{39}N_3O_9$ calcd. 657.27. found 656 [M−H]$^−$.

Gelates/thickens: 2-propanol, ethanol.

Synthesis of CHex-Am-Lys(BOC)-OH

Synthesis of CHex-Am-Leu-OMe

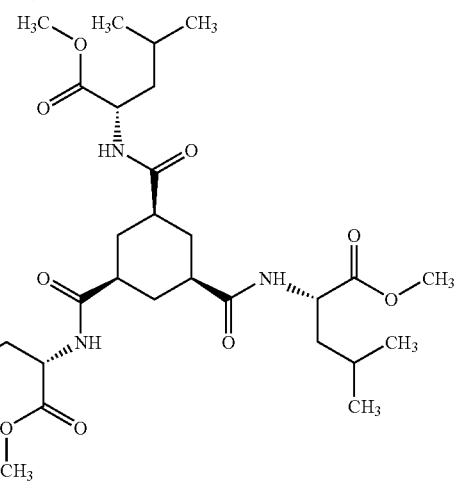

L-leucine methyl ester hydrochloride (1.90 g; 11.1 mmol; 3.0 eq)) in 50 ml dry $CH_2Cl_2$ was cooled to 0° C. and $Et_3N$

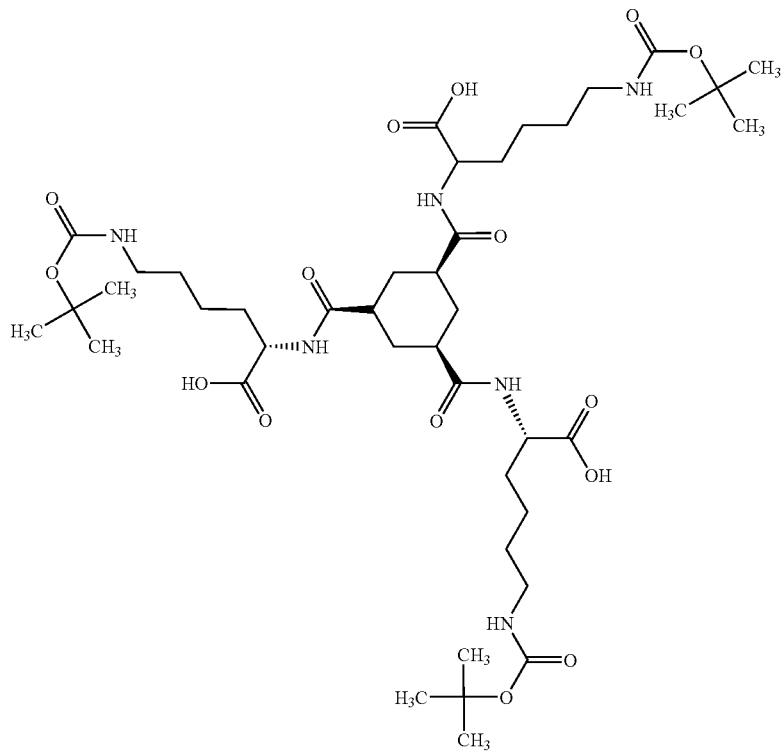

CHexAmLys(BOC)OMe (1.00 g; 1.1 mmol) was added to 20 ml MeOH. The mixture was cooled to 0° C. and NaOH (15 ml; 2 M) was added. The mixture was slowly brought back to room temperature and stirred for 20 hours. The solution was diluted with water (50 ml) and HCl (2M) was added till the pH was lower than 3. A precipitate appeared and this was filtered. The product was purified in EtOH and water. The product was dried in the vacuum oven. The yield is 87% (0.83 g; 0.9 mmol). $^1$H-NMR (DMSO): δ 1.31-1.68 (m, br, 17H); δ 2.30 (m, 1H); δ 2.87 (m, 2H, $CH_2NH$); δ 4.09 (m, 1H); δ 6.78 (m, 1H, NH); δ 7.99 (d, 1H, Ni).

Gelates/thickens: 1,2-dichloroethane.

(3.0 ml; 2.2 g; 22.2 mmol; 6.0 eq) was added. Cis,cis-1,3,5-cyclohexanetricarbonyl trichloride (1.00 g; 3.7 mmol; 1.0 eq) in 5 ml dry $CH_2Cl_2$ was added to the cooled solution. The mixture was slowly brought back to room temperature and left stirring overnight. When the reaction was stopped a precipitate was formed. This solid was collected by vacuum filtration. The precipitate was stirred in ethanol to remove any impurities. The product was collected by filtration. Recrystallization of the product in DMSO/ethanol was not successful. The yield was 28% (1.21 g, 2.1 mmol). $^1$H-NMR (DMSO): δ 0.88 (q, 6H); δ 1.41-1.76 (br, m, 5H); δ 3.64 (s, 5H); δ 4.29 (m, 1H); δ 8.19 (d, $^3$J=7.8 Hz, NH, 1H). $^{13}$C-NMR (DMSO): δ 20.09, 21.77, 23.31, 80.22, 41.26, 48.94, 50.78, 172.16, 178.38. Elemental Analysis for $C_{30}H_{51}N_3O_9$ (597.76). calcd. C, 60.28%; H, 8.60%; N, 7.03%; δ 24.09%.

found C, 60.21%; H, 8.69%; N, 7.01%. EI-MS for $C_{30}H_{51}N_3O_9$ calcd. 597.36. found 597 [M+].

Gelates/thickens: 2-octanol, 2-propanol

Synthesis of CHex-Am-Gly-OMe

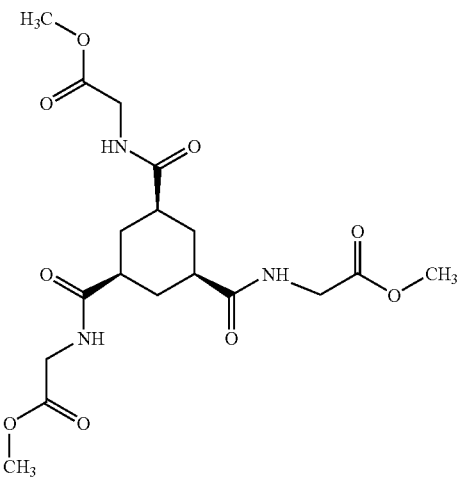

Glycine methyl ester hydrochloride (1.40 g; 11.1 mmol; 3.0 eq) in 50 ml dry $CH_2Cl_2$ was cooled to 0° C. and $Et_3N$ (8.0 ml; 2.2 g; 22.2 mmol; 6.0 eq) was added. Cis,cis-1,3,5-cyclohexanetricarbonyl trichloride (1.00 g; 3.7 mmol; 1.0 eq) in 5 ml dry $CH_2Cl_2$ was added to the cooled solution. The mixture was slowly brought back to room temperature and left stirring overnight. When the reaction was stopped a precipitate was formed. This solid was collected by vacuum filtration. The precipitate was stirred in ethanol to remove any impurities. The product wars collected by filtration. The product was recrystallized in DMSO/ethanol. The yield is 69% (2.44 g; 3.3 mmol). $^1$H-NMR (DMSO): δ 1.37 (t, 1H); δ 1.77 (d, $^3$J=12.2 Hz, 1H); δ 2.27 (t, 1H); δ 3.61 (s, 3H); δ 3.78 (d, $^3$J=5.9 Hz, 2H); δ 8.24 (t, NH, 1H). $^{13}$C-NMR (DMSO): δ 80.26, 41.16, 50.62, 169.43, 173.67. Elemental Analysis for $C_{18}H_{27}N_3O_9$ (429.43): calcd. C, 50.35%; H, 6.34%; N, 9.79%; δ 38.63%. found C, 60.38%; H, 6.56%; N, 9.60%. EI-MS for $C_{18}H_{27}N_3O_9$ calcd. 429.17. found 429 [M+].

Gelates/thickens: 2-octanol, 2-propanol, 1,2-dichloroethane.

Synthesis of CHex-Am-Phe-OMe (racemic)

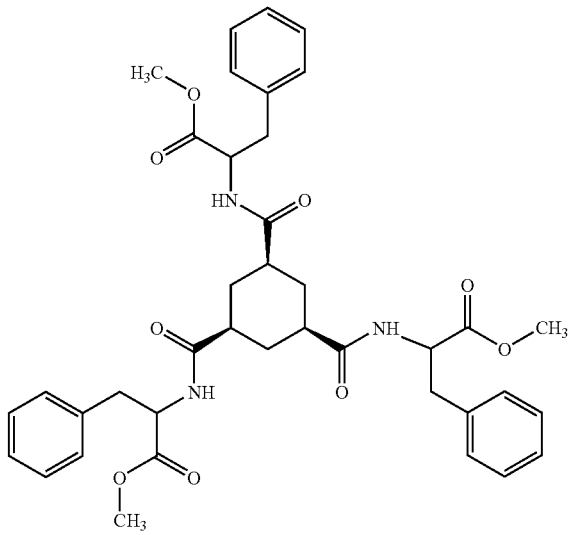

D-phenylalanine methyl ester hydrochloride [1.00 g] and L-phenylalanine methyl ester hydrochloride [0.90 g] (1.90 g; 11.3 mmol; 3.0 eq) stirred in 100 ml dry $CH_2Cl_2$ was cooled and was added $Et_3N$ (3.1 ml; 22.6 mmol; 6.0 eq). Added to the reaction mixture was cis,cis-1,3,5-benzenetricarbonyl trichloride (1.0 g; 3.8 mmol; 1.0 eq) in 10 ml dry $CH_2Cl_2$. The solution was slowly brought back to room temperature and left stirring overnight. The next morning a precipitate had formed. This solid was filtered and washed in ethanol, dried in the vacuum oven. The yield was 75% (1.98 g; 2.8 mmol). $^1$H-NMR (DMSO): δ 1.17-1.64 (m, br, 2H); 2.17 (s, br, 1H); δ2.90 (d, 1H, $CH_2$); δ 3.02 (m, 1H, $CH_2$); δ 3.60 (s, 3H, $OCH_3$); δ 4.45 (s, br, 1H); 7.21 (s, br, 5H, Ar); δ 8.22 (d, $^3$J=6.2 Hz, 1H, NH). $^{13}$C-NMR (DMSO): δ 35.48, 41.02, 50.81, 52.22, 125.45, 127.11, 127.97, 136.25, 171.13, 173.12.

Gelates/thickens: n-butylacetate, 2-octanol, ethanol, 2-propanol.

Synthesis of CHex-Am-Val-OMe

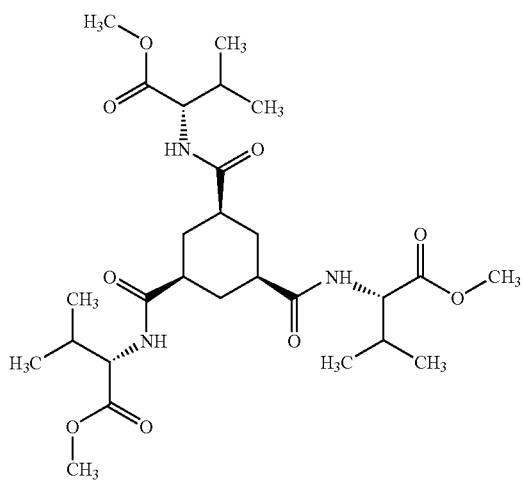

L-valine methyl ester hydrochloride (1.70 g; 11.1 mmol; 3.0 eq) in 50 ml dry $CH_2Cl_2$ was cooled to 0° C. and $Et_3N$ (3.0 ml; 2.2 g; 22.2 mmol; 6.0 eq) was added. Cis,cis-1,3,5-cyclohexanetricarbonyl trichloride (1.00 g, 3.7 mmol; 1.0 eq) in 5 ml dry $CH_2Cl_2$ was added to the cooled solution. The mixture was slowly brought back to room temperature and left stirring overnight. When the reaction was stopped a precipitate was formed. This solid was collected by vacuum filtration. The precipitate was stirred in ethanol to remove any impurities. The product was collected by filtration. The product was recrystallized in DMSO/ethanol. The yield is 51% (1.05 g; 1.9 mmol). $^1$H-NMR (DMSO): δ 0.88 (m, 6H); δ 1.43 (q, 1H); δ 1.69 (d, 1H); δ 2.05 (m, 1H); δ 3.65 (S, 3H); δ 4.19 (t, 1H); δ 8.11 (d, $^3$J=8.6 Hz, 1H, NH). $^{13}$C-NMR (DMSO): δ 17.20, 18.00, 28.83, 30.40, 40.94, 50.64, 56.03, 171.28, 173.67. Elemental analysis for $C_{27}H_{45}N_3O_9$ (555.67): calcd. C, 58.36%; H, 8.16%; N, 7.66%; O, 25.91%. found C, 58.21%; H, 8.22%; N, 7.46%. EI-MS for $C_{27}H_{45}N_3O_9$ calcd. 655.82. found 555 [M+].

Gelates/thickens: 2-octanol, ethanol 2-propanol.

Synthesis of CHex-Am-Lys(Boc)-OMe

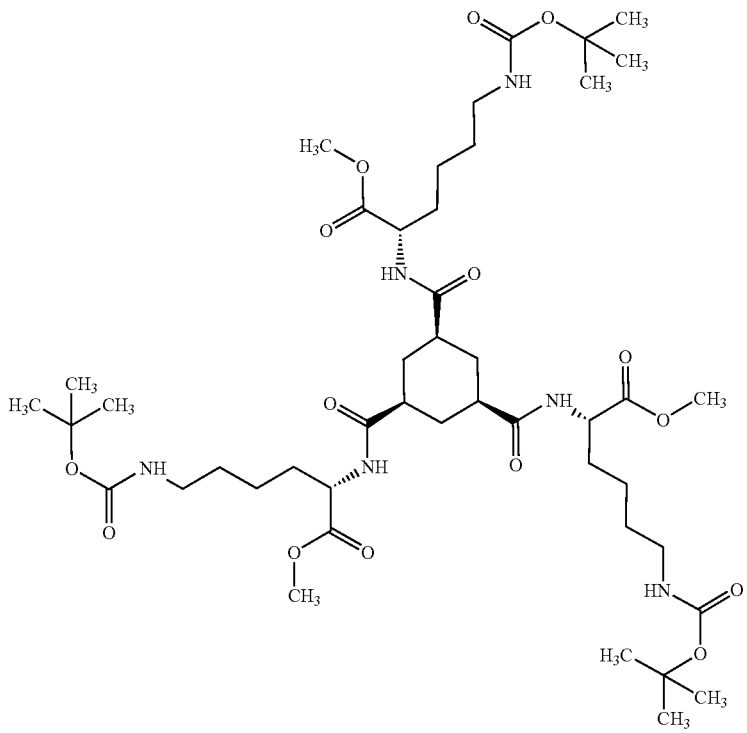

$N_e$—BOC-L-lysine methyl ester hydrochloride (2.50 g; 8.4 mmol; 3.0 eq) in 100 ml dry $CH_2Cl_2$ was cooled to 0° C. and $Et_3N$ (2.34 ml; 16.8 mmol; 6.0 eq) was added. Cis,cis-1, 3,5-cyclohexanetricarbonyl trichloride (0.76 g; 2.8 mmol, 1.0 eq) in 20 ml dry $CH_2Cl_2$ was added to the cooled solution. The mixture was slowly brought back to room temperature and left stirring overnight. When the reaction was stopped a precipitate had formed. This precipitation was filtered and recrystallized from ethanol to remove any impurities. The product was collected by filtration and dried in the vacuum oven. The yield was 65% (1.72 g; 1.8 mmol). EI-MS for $C_{46}H_{73}N_5O_{15}$ calcd. 942.55. found 943.6 [M+H$^+$].

Gelates/thickens: p-xylene, 2-octanol, 1,2-dichloroethane, 2-propanol.

Synthesis of CHexAmMetOH (1)

a) Synthesis of CHexAmMetOMe (2)

Cis,cis-1,3,5-cyclohexanetricarbonyl trichloride (1.40 g, 5.2 mmol) in dry $CH_2Cl_2$ (15 ml) was added to a solution of HCl.L-Met-OMe (3.20 g, 16.1 mmol) and $Et_3N$ (4.5 ml 32.8 mmol) in dry $CH_2Cl_2$ (200 mL, T=0° C.). The solution was slowly brought back to room temperature and left stirring overnight. The precipitate formed was filtered and washed with ethanol. The product dried in the vacuum oven. Yield: 2.96 g (4.54 mmol, 87%)

Gelates J thickens: n-butylacetate, 2-octanol, 1,2-dichloroethane, ethanol 2-propanol, water.

Synthesis of CHexAmMetOMe (racemic) (3)

3 was synthesized similarly to 2, starting from the racemic HCl.L-Met-OMe. Yield: 1.33 g (2.0 mmol; 47%)

Gelates/thickens: n-butylacetate, 2-octanol, 1,2-dichloroethane, water.

Synthesis of CHexAmMetOH (1)

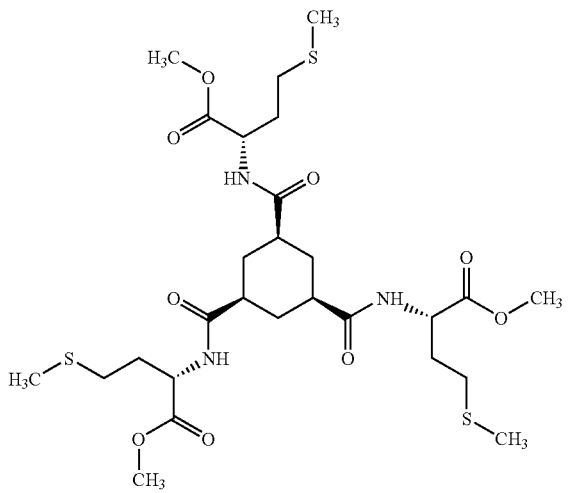

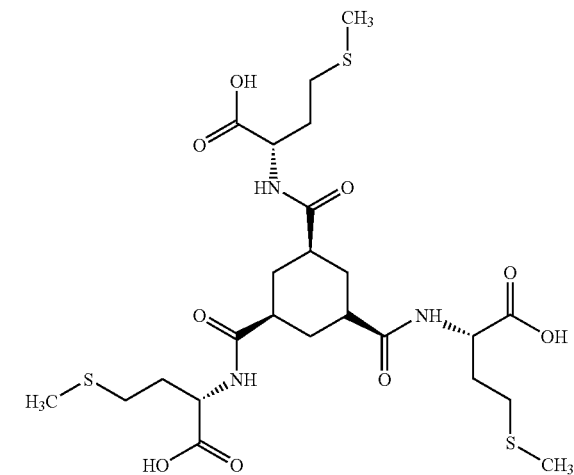

To a solution T=0° C.) of CHexAmMetOMe (2) (1.5 g, 2.3 mmol) in MeOH (30 ml) was added 2 M NaOH (15 ml). The mixture was slowly brought back to room temperature and stirred for 20 hours. The solution was diluted with water (60 ml) and 2 M HCl was added till pH<3. The precipitate formed was filtered and finally dried in the vacuum oven. Yield 1.27 g (2.10 mmol, 91%).

Gelates/thickens: ethanol, 2-propanol, water.

Synthesis of CHexAmPheOCH$_2$CH$_2$OH (4)

a) Synthesis of CHexAmPheOMe

Cis,cis-1,3,5-cyclohexanetricarbonyl trichloride (1.01 g, 3.7 mmol) in dry CH$_2$Cl$_2$ (5 ml) was added to HCl.L-Phe-OMe (1.90 g, 11.1 mmol) and Et$_3$N (3.0 ml, 22.2 mmol) in dry CH$_2$Cl$_2$ (50 mL, T=0° C.). The solution was slowly brought back to room temperature and left stirring overnight. The precipitate formed was collected by filtration and washed with ethanol and finally crystallized from DMSO/ethanol. Yield: 2.12 g (3.30 mmol, 82%)

b) Synthesis of CHexAmPheOH

CHexAmPheOMe (0.50 g, 0.71 mmol) was added to MeOH (10 ml) and 2 M NaOH (6 ml T=0° C.). The mixture was slowly brought back to room temperature and stirred for 20 hours. The solution was diluted with water (25 ml) and 2 M HCl was added till pH<3. The precipitate formed was filtered off and dried in the vacuum oven. Yield: 0.41 g (0.60 mmol, 84%)

c) Synthesis of CHexAmPheOCH$_2$CH$_2$OH (4)

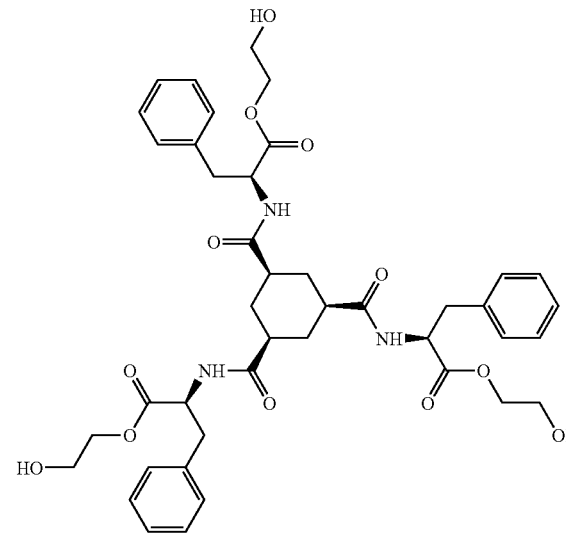

CHexAmPheOH (0.49 g, 0.74 mmol) was dissolved in ethylene glycol (60 ml). After addition of conc. HCl (3 drops) the solution was heated slowly till T=135° C. After 3 h the reaction mixture was cooled to T=−20° C. The precipitate formed was filtrated and washed with aceton. Yield 0.36 g (0.46 mmol, 59%)

Gelates/thickens: water.

Synthesis of CHexAmPheGlyOH (5)

c) Synthesis of Boc-L-Phe-Gly-OMe

Boc-L-Phe-Suc (1.81 g, 5.0 mmol), HCl.Gly-OMe (0.63 g, 5.0 mmol) and Et$_3$N (0.70 ml, 5.0 mmol) were dissolved in ethyl actetate (60 ml). After stirring for 20 h, the organic layer was washed with H$_2$O (60 ml), sat. NaHCO$_3$ (60 ml) and brine (60 ml) and dried with MgSO$_4$. After filtration and evaporation of the solvent the residue was purified by column chromatography (Silica, CH$_2$Cl$_2$-CH$_2$Cl$_2$MeOH 100:5). Yield 1.55 g (4.61 mmol, 92%)

b) Synthesis of TFA.L-Phe-Gly-OMe

Boc-L-Phe-Gly-OMe (1.55 g, 4.61 mmol) was dissolved in 2M TFA/CH$_2$Cl$_2$ (30 ml). After 4 h stirring, the solvents were evaporated and the residue was dried under high vacuum (0.1 mm Hg). Yield 2.13 g (contaminated with free TFA, about 4.56 mmol).

c) Synthesis of CHexAmPheGlyOMe

Cis,cis-1,3,6-cyclohexanetricarbonyl trichloride (0.40 g, 1.47 mmol) in dry CH$_2$Cl$_2$ (15 ml) was added to TFA.L-Phe-Gly-OMe (about 4.61 mmol, contaminated with approximately 4.56 mmol TFA) and Et$_3$N (1.91 ml, 13.8 mmol) in dry CH$_2$Cl$_2$ (30 ml, T=0° C.). The solution was slowly brought back to room temperature and left sting overnight. The precipitate formed was collected by filtration and washed with ethanol. Yield: 0.80 g (0.92 mmol, 62%)

d) Synthesis of CHexAmPheGlyOH (5)

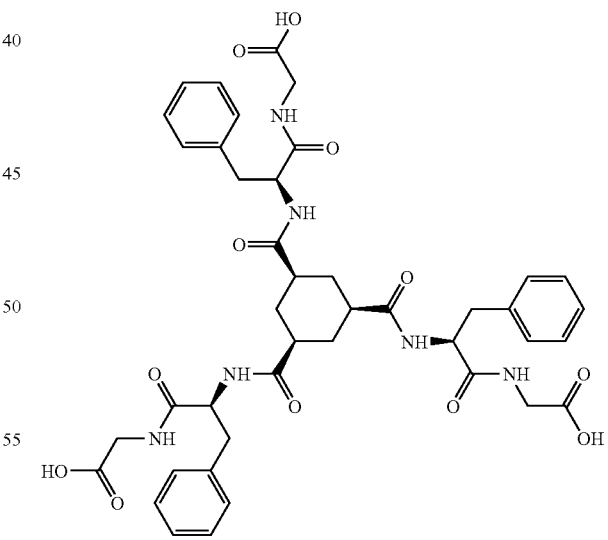

CHexAmPheGlyOMe (0.42 g, 0.48 mmol) was added to MeOH (15 ml) and 2 M NaOH (7.5 ml, T=0° C.). The mixture was slowly brought back to room temperature and stirred for 72 hours. The solution was diluted with water (25 ml) and 2 M HCl was added till pH<3. The precipitate formed was filtered off and dried in the vacuum oven. Yield: 0.34 g (0.41 mmol 85%) Gelates/thickens: water.

31

Synthesis of CHexAmPheNHCH₂CH₂OCH₂CH₂OH (6)

a) Synthesis of Boc-L-PheNHCH₂CH₂OCH₂CH₂OH

2(-2-aminoethoxy)-1-ethanol (0.72 g, 6.9 mmol) and Et₃N (0.96 ml, 6.9 mmol) were dissolved in ethyl acetate (60 ml). Subsequently, BOC-L-Phe-Suc (2.50 g, 6.9 mmol) in ethyl acetate (50 ml) was added to the reaction mixture. After stirring for 20 h, the organic solvent was extracted with H₂O, 10% NaHCO₃, H₂O, brine and dried over MgSO₄. After filtration, ethyl acetate was evaporated in vacuo. Yield 1.55 g (4.40 mmol; 64%)

b) Synthesis of TFA.L-PheNHCH₂CH₃OCH₃CH₂OH

Boc-L-PheNHCH₂CH₂OCH₂CH₂OH (1.55 g, 4.4 mmol) was dissolved in 2M TFA/CH₂Cl₂ (115 ml). After 4 h stirring, the solvents were evaporated and the residue was dried under high vacuum (0.1 m Hg). Yield 3.01 g (contaminated with free TFA, about 12.2 mmol).

c) Synthesis of CHexAmPheNHCH₂CH₂OCH₂CH₂OH (6)

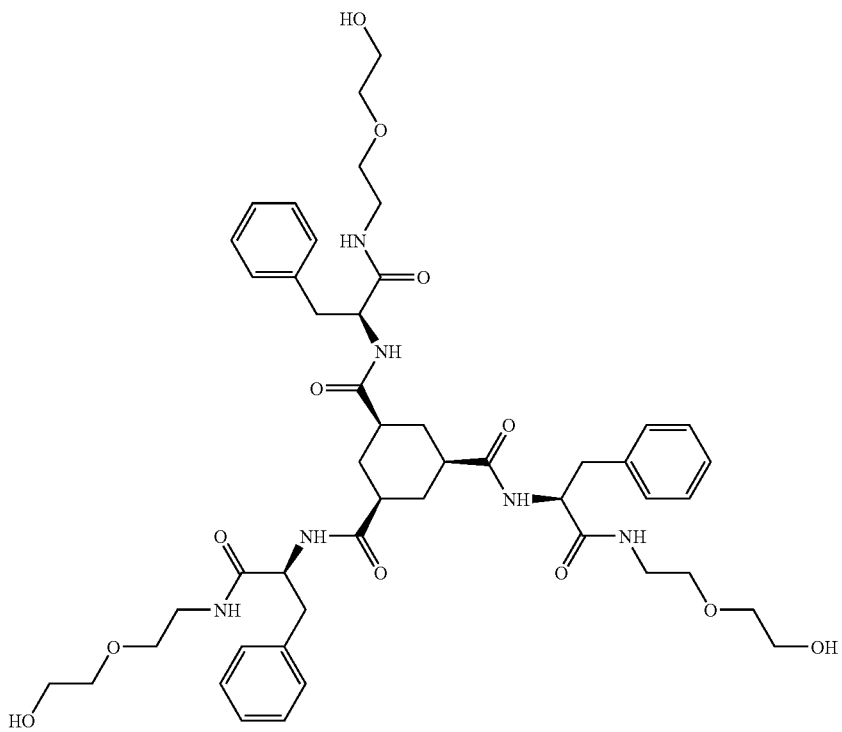

Cis,cis-1,3,5-cyclohexanetricarbonyl trichloride (0.40 g, 1.47 mmol) in dry CH₂Cl₂ (5 ml) was added to TFA.L-PheNHCH₂CH₂OCH₂CH₂OH (3.01 g, about 4.40 mmol, contaminated with approximately 12.2 mmol TFA) and Et₃N (2.9 ml, 20.8 mmol) in dry CH₂Cl₂ (100 ml, T=0° C.). The solution was slowly brought back to room temperature and left stirring overnight. The precipitate formed was collected by filtration, washed with ethanol and recrystallized from water. Yield: 0.78 g (0.86 mmol, 57%)

Gelates/thickens: ethanol, water.

32

Synthesis of CHexAmGluOMe (7)

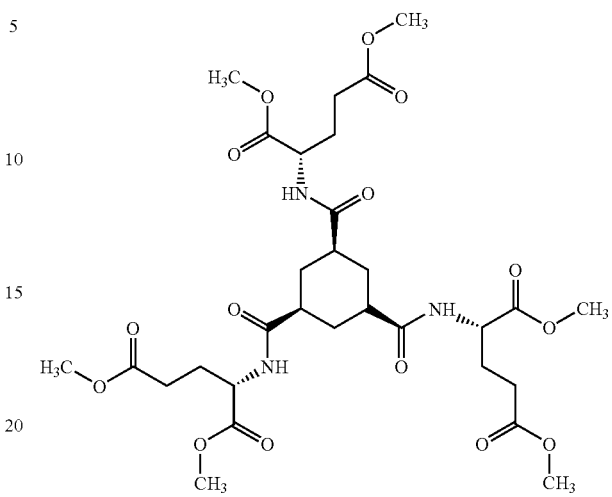

L-glutamic acid methyl ester hydrochloride (4.70 g; 22.1 mmol; 3.0 eq) in 200 ml dry CH₂Cl₂ was cooled to 0° C. and Et₃N (6.2 ml; 44.2 mmol; 6.0 eq) was added. Cis,cis-1,3,5-cyclohexanetricarbonyl trichloride (2.00 g; 7.4 mmol; 1.0 eq) in 15 ml dry CH₂Cl₂ was added to the cooled solution and the mixture was slowly brought back to room temperature and left stirring overnight. When the reaction was stopped a 'gel-like' precipitate was formed. This solid was collected by vacuum filtration. The precipitate formed a gel with MeOH, EtOH, H₂O and CH₂Cl₂. The precipitate was recrystallized in ether, filtered and dried in the oven for at least one week. Yield: 1.50 g (2.2 mmol 30%).

Gelates/thickens: n-butylacetate, 2-octanol 1,2-dichloroethane, ethanol, 2-propanol water.

Synthesis of CHexAmAspOMe (8)

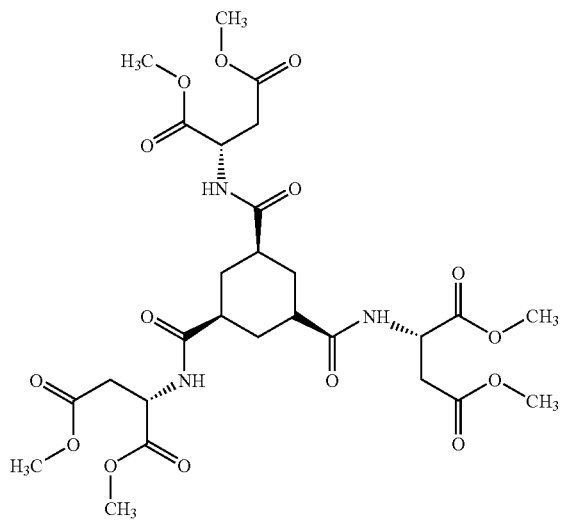

L-aspartic acid methyl ester hydrochloride (1.70 g; 8.4 mmol; 3.0 eq) in 200 ml dry $CH_2Cl_2$ was cooled to 0° C. and $Et_3N$ (2.3 ml; 16.6 mmol; 6.0 eq) was added. Cis,cis-1,3,5-cyclohexanetricarbonyl trichloride (0.76 g; 2.8 mmol; 1.0 eq) in 20 ml dry $CH_2Cl_2$ was added to the cooled solution and the mixture was slowly brought back to room temperature and left stirring for forty hours. Acetone was added and the precipitate was filtered and dried in the oven. The precipitate was recrystallized in ethanol, filtered and dried in the oven. Yield: 0.92 g (1.4 mmol; 51%).

Gelates/thickens: n-butylacetate, 2 octanol 1,2-dichloroethane, ethanol, 2-propanol, water, water/ethanol mixtures.

Synthesis of CHexAmPheOH (racemic) (9)

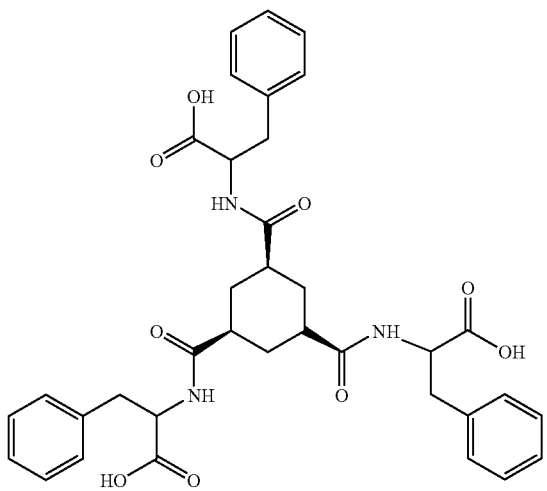

Racemic CHexAmPheOMe (0.65 g) was added to 20 ml MeOH and stirred. The mixture was cooled and NaOH (15 ml; 2 M) was added. The mixture was slowly brought back to r.t. and stirred for 20 hours. The solution was diluted with water (75 ml) and 2 M HCl was added till the pH was lower than 3. The precipitate was filtered and dried in the vacuum over. Yield: 0.42 g (0.6 mmol; 69%).

Gelates/thickens: water.

Synthesis of CHexAmPheOH (DDL) (10)

a) Synthesis of CHexAmPheAm-(1,4)-ArNO$_3$ (DDL)

CHexAm(L)PheAm-(1,4)-ArNO$_2$ (0.50 g; 1.0 mmol; 1.0 eq), D-phenylalanine methyl ester hydrochloride (0.46 g; 2.1 mmol; 2.1 eq), DMT-MM (0.61 g; 2.2 mmol; 2.2 eq) and $Et_3N$ (0.29 ml; 0.21 g; 2.1 mmol; 2.1 eq) were stirred in 50 ml MeOH overnight. The next morning app. 20 ml ethanol was added and the mixture was stirred for a further 15 minutes. The remaining precipitate was filtered and dried in the vacuum oven. Yield: 0.50 g (0.6 mmol; 59%).

b) Synthesis of CHexAmPheOH (DDL) (10)

CHexAm-(2×D)-PheOMe-(1×L)-PheAm-(1,4)-ArNO$_2$ (0.50 g; 0.6 mmol; 1.0 eq) was stirred in 15 ml MeOH and NaOH (10 ml; 2M) was added. The reaction was stirred for two days. At the end of the reaction the mixture had turned bright yellow. 2M HCl was added till the pH was 2 and a precipitate formed. The precipitate was filtered and washed with water till the precipitate and the filtrate were no longer yellow. The product was dried in the oven. Yield: 0.42 g (0.6 mmol; 97%).

Gelates/thickens: water.

Synthesis of CHexAm(L)Phe(D)AlaOH (11)

a) Synthesis of TFA-H$_3$N$^+$-(L)Phe(D)AlaOMe

BOC-(L)Phe(D)AlaOMe (2.69 g; 7.7 mmol; 1.0 eq) was dissolved in 25 ml $CH_2Cl_2$ and 15 ml TFA in 75 ml $CH_2Cl_2$ were added. The mixture was stirred for three hours. Solvent and excess TFA were evaporated in vacuo, yielding 4.83 g TFA-H$_3$N$^+$-(L)Phe(D)AlaOMe and excess TFA, which could not be evaporated. The product was used in the next step without further purification.

b) Synthesis of CHexAm(L)Phe(D)AlaOMe

TFA-H$_3$N$^+$-(L)Phe(D)AlaOMe (4.83 g) in 100 ml dry $CH_2Cl_2$ was cooled and $Et_3N$ (4.70 ml; 3.42 g; 33.8 mmol) was added. Cis,cis-1,3,5-cyclo hexanetricarbonyl trichloride (0.7 g; 2.6 mmol; 1.0 eq) in 5 ml dry $CH_2Cl_2$ was added to the reaction mixture. The solution was slowly brought back to room temperature and left stirring overnight. The next morning ethanol was added to the mixture and the remaining precipitate was filtered and dried in the oven. The product was used in the next step without further drying or purification. Yield: 4.5 g (wet).

c) Synthesis of CHexAm(L)Phe(D)AlaOH (11)

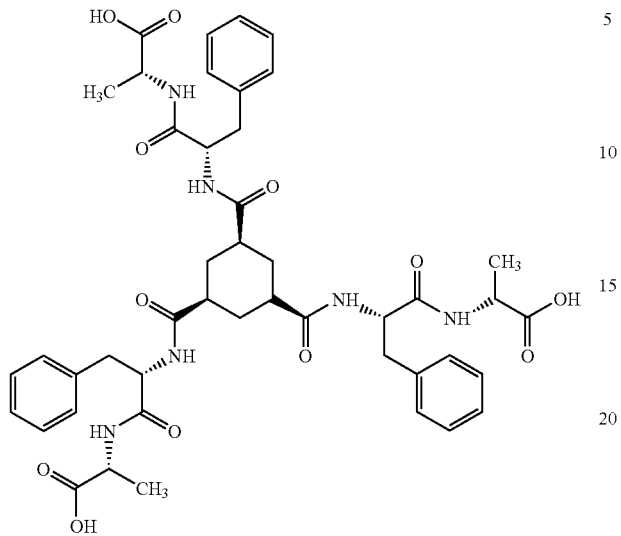

4.5 g (wet) CHexAm(L)Phe(D)AlaOMe was stirred in 50 ml MeOH, 2M NaOH (15 ml) was added and the reaction was stirred overnight. The next day 50 ml $H_2O$ and 50 ml MeOH were added and the pH was brought to 2 with 2M HCl. The formed precipitate was filtered, washed with MeOH and dried in the vacuum oven. The obtained product was dissolved in app. 3 ml NaOH (2M). EtOH (30 ml) was added after which a gel formed. The gel was filtered and the solid was dissolved in 1 ml 2M NaOH. To this solution app. 4 ml MeOH and 5 ml $H_2O$ was added, then app. 2 ml 2M HCl was added till pH 4. The precipitate was filtered and dried in the vacuum oven. Yield: 0.54 g (0.6 mmol; 24%).

Gelates/thickens: ethanol, water.

Synthesis of CHexAm(L)Phe(β)AlaOH (12)

a) Synthesis of BOC-(L)Phe(β) AlaOMe

BOC-Phe-Suc (2.51 g; 6.9 mmol; 1.0 eq) and β-alanine methyl ester hydrochloride (0.96 g; 6.9 mmol; 1.0 eq) were stirred at r.t. in 50 ml ethyl acetate and $Et_3N$ (1.92 ml; 1.40 g; 13.8 mmol; 2.0 eq) overnight. The next day the formed precipitate ($Et_3N$*HCl) was filtered off. The organic solvent was extracted with $H_2O$, 10% $NaHCO_3$, $H_2O$, Brine and dried over $MgSO_4$. Ethyl acetate was evaporated in vacuo, giving BOC-(L)Phe(β)AlaOMe. The product was used in the next step without farther purification.

Yield: 2.10 g (6.0 mmol; 87%).

b) Synthesis of TFA $H_3N^+$-(β)Phe(β)AlaOMe

BOC-(L)Phe(β)AlaOMe (2.10 g; 6.0 mmol; 1.0 eq) was stirred for three hours in 100 ml $CH_2Cl_2$ and 15 ml TFA. Solvent and excess TFA were evaporated in vacuo, yielding 4.63 g $TFA^+H_3N^-$-(L)Phe(β)AlaOMe and excess TFA, which could not be evaporated. The product was used without further purification for the next reaction step.

c) Synthesis of CHexAm(L)Phe(β)AlaOMe $TFA^-H_3N^+$-(L)Phe(β)AlaOMe (4.68 g) in 100 ml dry $CH_2Cl_2$ was cooled and $Et_3N$ (7.00 ml; 5.09 g; 50.3 mmol; excess) was added. Cis,cis-1,3,5-cyclo-hexanetricarbonyl trichloride (0.45 g; 1.7 mmol; 1.0 eq) in 10 ml dry $CH_2Cl_2$ was added to the reaction mixture. The solution was slowly brought back to room temperature and left stirring overnight. The next morning ethanol was added to the mixture and the remaining precipitate was filtered and dried in the oven. The product was CHexAm(L)Phe(β)AlaOMe and the yield was not determined. The product was used in the next step without further drying or purification.

d) Synthesis of CHexAm(L)Phe(β)AlaOH (12)

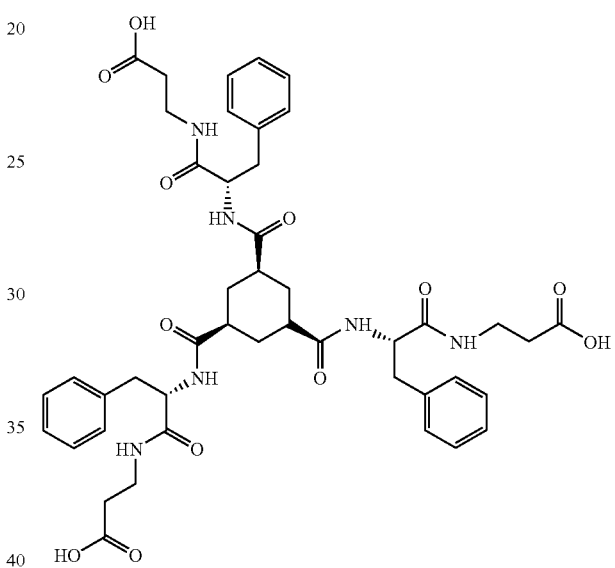

All the product made in the previous step (CHexAm(L)Phe(β)AlaOMe) was stirred in 5 ml MeOH and NaOH (10 ml; 2M) overnight. The next day 15 ml MeOH and NaOH (10 ml; 2M) were added and the reaction was again stirred overnight. The next day the mixture was filtered, after which water (app. 50 ml) was added. The pH was brought to 2 with 2M HCl. The formed precipitate was filtered and dried in the vacuum oven to give pure CHexAm(L)Phe(β)AlaOH. Yield: 1.18 g (1.4 mmol; 80%).

Gelates/thickens: water.

Synthesis of CHexAmPheAmGluOH (13)

a) Synthesis of BOC-PheAmGluOMe

L-BOC-Phe-Suc (2.50 g; 6.9 mmol; 1.0 eq) and L-Glutamic acid dimethyl ester hydrochloride (1.5 g; 7.1 mmol; 1.1 eq) were stirred at r.t. in 50 ml ethyl acetate and $Et_3N$ (1.92 ml; 1.40 g; 13.8 mmol; 2.0 eq) overnight. The next day the formed precipitate ($Et_3N$*HCl) was filtered off. The organic solvent was extracted with $H_2O$, 10% $NaHCO_3$, $H_2O$, Brine and dried over $MgSO_4$. Ethyl acetate was evaporated in vacuo, BOC-PheAmGluOMe. The product was used in the next step without further purification. Yield: 2.53 g (6.4 mmol; 93%).

b) Synthesis of TFA⁻H₃N⁺-PheAmGluOMe

BOC-PheAmGluOMe (2.53 g; mmol; 1.0 eq) was stirred for three hours in 60 ml CH₂Cl₂ and 10 ml TFA. Solvent and excess TFA were evaporated in vacuo, yielding 4.91 g TFA⁺H₃N⁻-PheAmGluOMe and excess TFA, which could not be evaporated.

c) Synthesis of CHexAmPheAmGluOMe

TFA⁻H₃N⁺-PheAmGluOMe (4.91 g) in 60 ml dry CH₂Cl₂ was cooled and Et₃N (5.00 ml; 3.64 g; 35.9 mmol; excess) was slowly added. Cis,cis-1,3,5-cyclo-hexanetricarbonyl trichloride (0.48 g; 1.8 mmol; 1.0 eq) in 10 ml dry CH₂Cl₂ was slowly added to the reaction mixture. The solution was slowly brought back to room temperature and left stirring overnight. The next morning ethanol was added to the mixture. After 15 minutes of stirring, the remaining precipitate was filtered and dried in the oven. The product was CHexAmPheAmGluOMe and the yield was not determined, but 0.32 g (0.3 mmol) CHexAmPheAmGluOMe was obtained. The product was used in the next step.

d) Synthesis of CHexAmPheAmGluOH (13)

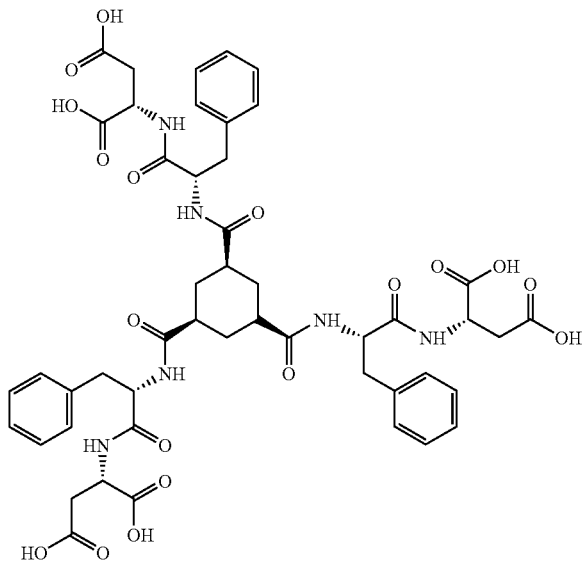

All the product minus 0.82 g made in the previous step was stirred in 50 ml MeOH and NaOH (20 ml; 2M) overnight. The next day 5 ml EtOH and water (app. 50 ml) was added. The pH was brought to 2 with 2M HCl. The formed precipitate was filtered and dried in the vacuum oven. The product was recrystalised twice by dissolving it in NaOH and precipitating it by acidification with HCl. The precipitate was filtered off and dried to give pure CHexAmPheAmGluOH. Yield: 0.47 g (0.47 mmol; 31%).

Gelates/thickens: water.

Synthesis of CHeAmMetAmCH₂Pyr (14)

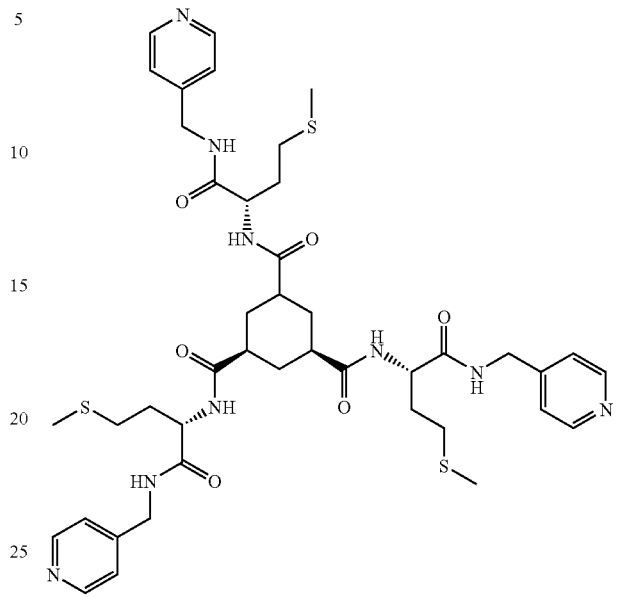

a) A solution of Boc-L-Met (3.0 g, 12.04 mmol), 4-aminomethyl pyridine (1.4 g, 18.24 mmol), and DMT-MM (3.7 g, 13.24 mmol) in methanol (50 mL) was stirred overnight at room temperature, after which the solvent was evaporated. The resulting mixture was dissolved in ethyl acetate and water (150 mL each) and brine (100 mL) was added to improve the separation of the layers. The ethyl acetate layer was washed with brine (2×150 mL), water (2×150 mL), and brine (150 mL), after which it was dried with Na₂SO₄ and evaporated to dryness, The resultant solid was purified by column chromatography (SiO₂, CH₂Cl₂:hexanes=1:1, going to CH₂Cl₂, going to CH₂Cl₂:methanol=97:3. Yield: 1.3 g (32%).

b) The product synthesized under a) (1.3 g, 8.84 mmol) was dissolved in CH₂Cl₂ (100 mL) to which trifluoroacetic acid (10 mL) and DMF (1 drop) were added. After stirring at room temperature for 3 h the solution was evaporated to dryness and the resultant blue oil was used for the next reaction without any further purification. Yield 2.2 g.

c) To a cooled (0° C.) solution of the product synthesized under b) (2.2 g, 3.84 mmol) and Et₃N (3 mL, excess) in CH₂Cl₂ (100 mL), was added dropwise a solution of cis,cis-1,3,5-cyclohexanetriacid chloride (0.27 g, 1.0 mmol). The solution was stirred overnight while being allowed to came to room temperature. Meanwhile an orange, gel-like substance had formed, which was filtered off, washed with CH₂Cl₂, MeOH, H₂O/MeOH, and Et₂₀ (ca. 20 mL each) and subsequently dried. The resultant solid was dissolved in 1 N HCl and reprecipitated/regelled by addition of 2 N NaOH Filtration of the precipitate/gel, followed by drying gave the desired product. Yield 0.2 g (23.7% based on the cis,cis-1,3, 5-cyclohexanetriacid chloride).

Gelates/thickens: water/methanol and water/ethanol mixtures.

Synthesis of CHexAmMetHisOMe (15)

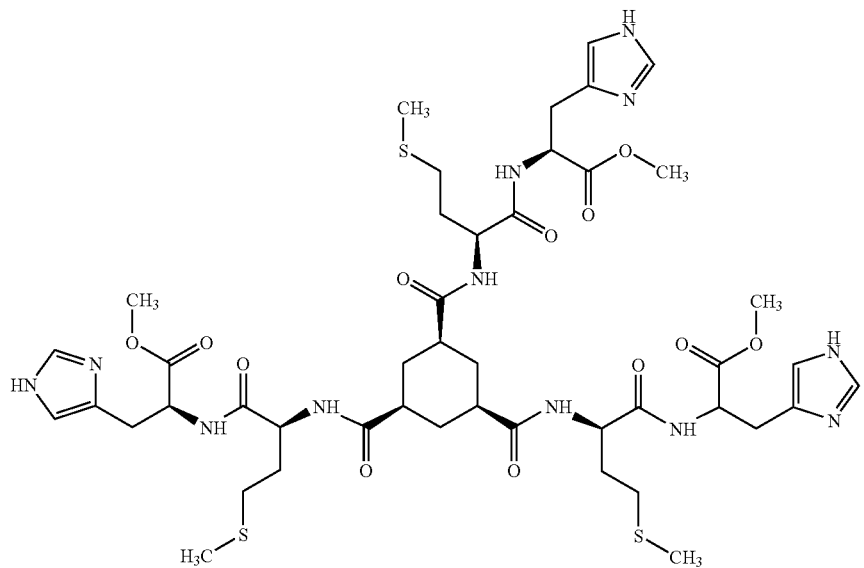

(MetHisOMe was synthesized following standard peptide chemistry protocols) MetHisOMe (2.76 g; 9.23 mmol) containing a calculated amount of 14 mmol (1.6 g) TFA was dissolved in 100 ml $CH_2Cl_2$ and cooled to 0° C. $Et_3N$ (2.8 ml=20 mmol) was added to neutralize the traces of TFA. Cis,cis-1,3,5-cyclohexane tricarbonyl trichloride (0.35 g; 1.30 mmol) was added, after which the temperature was slowly brought back to RT. After reacting for 1 night at RT the formed precipitate was collected by filtration and dried in vacuo. Yield: 43.2%

Gelates/thickens: ethanol, 2-propanol, water.

Synthesis of CHexAmMetHista (16)

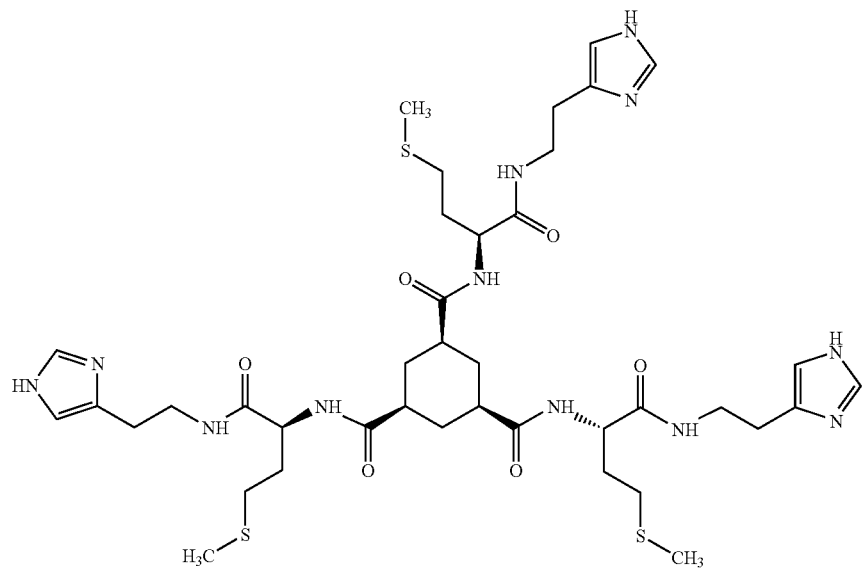

A mixture of CHexAmMetOH (1) (1.0 g; 1.64 mmol), carbodiimidazole (0.82 g; 5.1 mmol) and Et₃N (0.82 ml; 5.9 mmol) was stirred at RT for 1 hour. Histamine dihydrochloride (0.94 g; 5.1 mmol) in 20 ml of DMSO was added dropwise. After reacting for 1 night at RT an excess of H₂O was added and the formed precipitate was collected by filtration and dried in vacuo, Yield: 660 mg; 45%.

Gelates/thickens: ethanol, 2-propanol, water.

Synthesis of CHexAmPheOCH₂CH₂OCH₂CH₂OH (17)

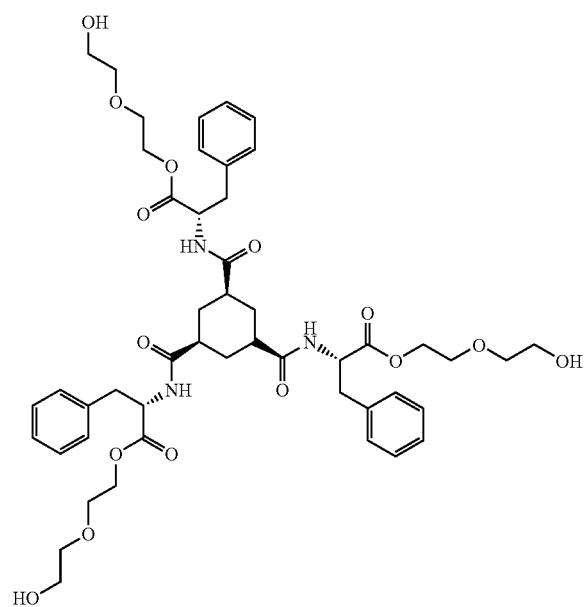

17 was synthesized similarly to 4, using diethyleneglycole. Yield: 2.01 g (2.18 mmol; 75.4%)

Gelates/thickens: water.

Synthesis of CHexAmValOH (18)

a) Synthesis of CHexAmValOMe

L-valine methyl ester hydrochloride (1.70 g; 11.1 mmol; 3.0 eq) in 50 ml dry CH₂Cl₂ was cooled to 0° C. and Et₃N (3.0 ml; 2.2 g; 22.2 mmol; 6.0 eq) was added. Cis,cis-1,3,5-cyclohexanetricarbonyl trichloride (1.00 g; 3.7 mmol; 1.0 eq) in 5 ml dry CH₂Cl₂ was added to the cooled solution. The mixture was slowly brought back to room temperature and left stirring overnight. When the reaction was stopped a precipitate was formed. This solid was collected by vacuum filtration. The precipitate was stirred in ethanol to remove any impurities. The product was collected by filtration. The product was recrystallized in DMSO/ethanol. The yield is 51% (1.05 g; 1.9 mmol).

Synthesis of CHexAmValOH (18)

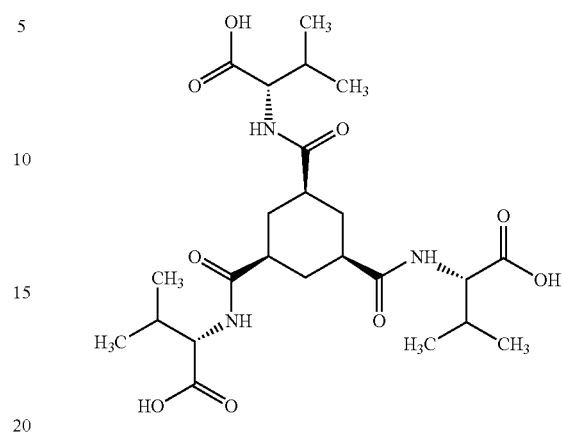

cHexAmValOMe (0.54 g; 1.0 mmol) was added to 10 ml MeOH. The mixture was cooled and NaOH (5 ml; 2 M) was added. The mixture was slowly brought back to room temperature and stirred for 20 hours. The solution was diluted with water (25 ml) and 2 M HCl was added till the pH was lower than 3. The product precipitated and was dried in the vacuum oven. The yield is 24% (0.12 g; 0.2 mmol).

Gelates/thickens: water.

Synthesis of CHexMetAmBorate (19)

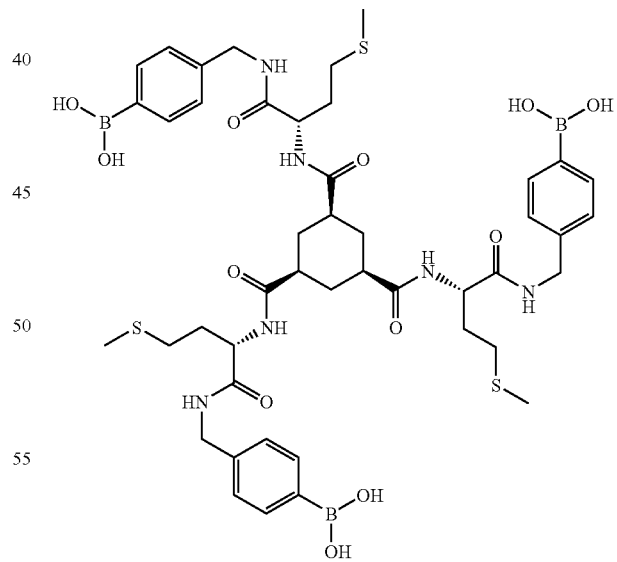

19 was synthesize similarly to 6, using methionine as the amino acid and 3-aminomethylphenyl)boronic acid hydrochloride instead of 2(-2-aminoethoxy)-1-ethanol.

Gelates/thickens: water.

Synthesis of CHexAmPheAmBorate (20)

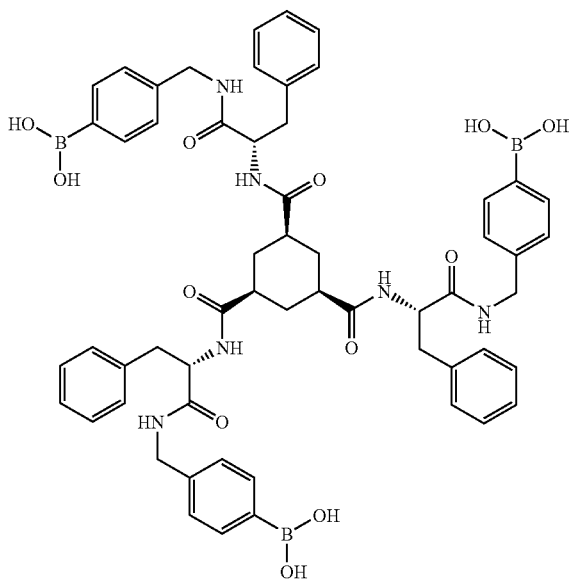

20 was synthesized similarly to 6, sing 3-aminomethylphenyl)boronic acid hydrochloride instead of 2(-2-aminoethoxy)-1-ethanol.

Gelates/thickens: water.

Synthesis of CHexAmSer(Bzl)AmBorate (21)

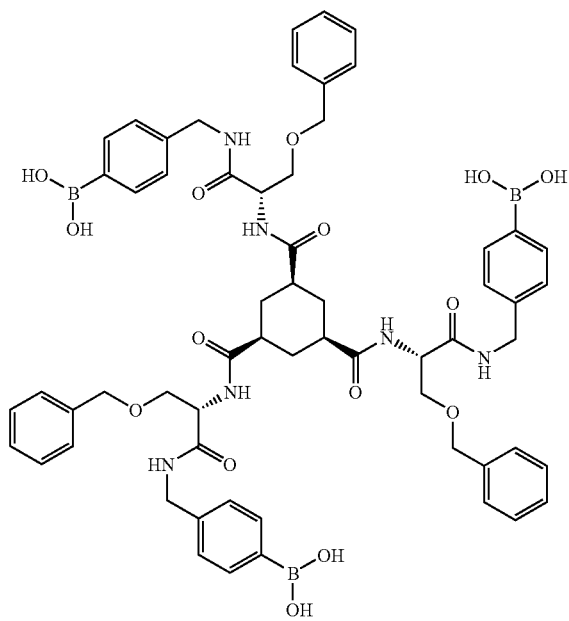

21 was synthesized similarly to 6, using benzylserine as the amino acid 3-aminomethylphenyl)boronic acid hydrochloride instead of 2(-2-aminoethoxy)-1-ethanol.

Gelates/thickens: water.

Gelation Experiments

A weighted amount of solid was dissolved in 0.5 or 1 ml of the solvent in a closed 1.5 ml vial using a heating gun or a heating block and subsequently slowly cooled to room temperature by standing in the air. Gelation was determined by turning the vial upside down and gentle shaking. If no flow of the mass was observed, the mass was defined to be a gel. Alternatively, a weighed amount of solid was dissolved in 1 mL of solvent by the addition of acid or base. The subsequent addition of base or acid then gave gelation. Alternatively, a weighed amount of solid was dissolved in a small amount of solvent. The subsequent addition of a large amount of non-solvent then gave gelation.

Melting temperatures of the gels ($T_{gel}$) were determined by the dropping ball method (H. M. Tan, A. Moet, A. Hiltner, E. Baer, Macromolecules 1983, 16, 28).

Metathesis reaction on MdL059

In flame dried glassware a viscous solution was made of MdL059 (100 mg, 0.094 mmol) in dry benzene (10 ml) and placed under a nitrogen atmosphere. Into this solution was quickly mixed the Grubbs-catalyst (~14 mg, ~0.017 mmol) and the mixture was allowed to stand for 3 nights without stirring. After reaction, the obtained stiff gel was washed with benzene/1-hexene, to remove the remainder of the catalyst.

Transmission Electron, Microscopy Measurements

A gel was prepared following the procedure as described above. A small amount of the gel was carefully deposited on a Collidon/Carbon coated grid, using a small wooden stick. The samples were all prepared in duplo. The grids were carefully placed on a plate which was then mounted in the evaporator. Between the electrodes a bent wolfram wire was connected, around which a short piece of plating wire was wound. The following settings were used: distance between electrodes and grids: circa 15 cm; angle of evaporation: between 10° and 45°. Platinum was evaporated at a pressure of $10^{-5}$ mmHg. The samples were examined using a JEOL 1200EX (80-100 kV) and pictures were taken of representative parts. Alternatively, samples were investigated without shadowing.

Gelation of Mixtures of Gelators & Mixtures of Gelators and Structurally Alike Non-Gelators Mixed gels were prepared of the gelators CHexAmPheNHCH$_2$CH$_2$OCH$_2$CH$_2$OH and CHexAmPheOCH$_3$CH$_2$OH. The total wt % of gelator was kept constant at 0.1 wt % (1 mg/ml), but the ratio of the two gelators was varied from 0 to 100%. Gelation was observed for all mixtures.

Mixed gels were prepared of the gelators CHexAmPheNHCH$_2$CH$_2$OCH$_2$CH$_2$OH, CHexAmPheOCH$_2$CH$_2$OH, and CHexAmMetOH each in the presence of up to ca. 2 eq. underlying compound that is similar in structure but is water soluble. Stabile gels were obtained in all cases.

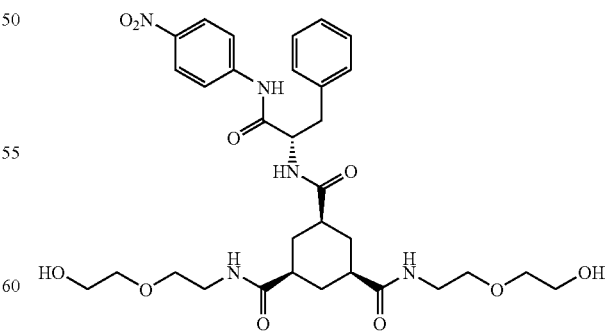

Use of a gel matrix for the entrapment of hydrophobic molecules/small crystallites of these molecules Pyrene and hydrogelator CHexAmPheOCH$_2$CH$_2$OCH$_2$CH$_2$OH were dissolved in a small amount of DMSO (100 μL). Upon the rapid addition of water (900 μL) instantaneous gelation took place. Due to the formation of small pyrene crystallites the sample had turned turbid (clear samples were obtained in the absence of pyrene). TEM investigation confirmed the formation of small crystallites (maximum observed size: ca 70 nm). Using this method Ca 4 mg of pyrene was entrapped in 1 ml of a 0.5 wt % gel of CHexAmPheOCH$_2$CH$_2$OCH$_2$CH$_2$OH.

The invention claimed is:

1. A gelling agent or thickener having the formula

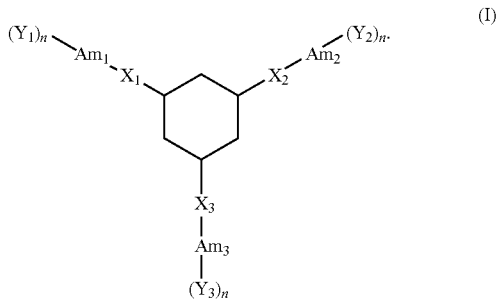

wherein
each of $X_1$, $X_2$ and $X_3$ is independently chosen from the moieties —NH, C(O)—, and —NH—C(O)—;
each of $Am_1$, $Am_2$, and $Am_3$ is independently a moiety based on an amino acid or a derivative thereof, or a number of amino acids or derivatives thereof;
each of $Y_1$, $Y_2$, and $Y_3$ is independently chosen from the group of —OR, —N(OH)R, and —NR$_2$, if the corresponding X ($X_1$ for $Y_1$, $X_2$ for $Y_2$, and $X_3$ for $Y_3$) is C(O)— or —NH—C(O)— and n=1, and each of $Y_1$, $Y_2$, and $Y_3$ is independently chosen from the group of C(O)R, —C(O)—NR$_2$, —C(O)—OR, C(S)R, —C(S)—NR$_2$, —C(S)—OR and R, if the corresponding X ($X_1$ for $Y_1$, $X_2$ for $Y_2$, and $X_3$ for $Y_3$) is —NH— and n=1 or 2, wherein each R is independently H, or a branched, cyclic or straight alkyl, alkenyl or alkynyl group which is optionally substituted with an aromatic, ester or ether moiety or one or more other heteroatoms and may have from 1 to 40 carbon atoms, with the proviso that the one or more heteroatoms are all selected from O, N, S, P and B; and
n=1 or 2.

2. A gelling agent or thickener according to claim 1, wherein $X_1$, $X_2$ and $X_3$ are the same.

3. A gelling agent or thickener according to claim 1, wherein $Am_1$, $Am_2$, and $Am_3$ are the same.

4. A gelling agent or thickener according to claim 1, wherein $Y_1$, $Y_2$, and $Y_3$ are the same.

5. A gelling agent or thickener according to claim 4, wherein $Y_1$, $Y_2$ and $Y_3$ are chosen from the group of —OH, —OCH$_3$, —OCH$_2$CH$_3$, —OCH$_2$CH$_2$OH, —NH$_2$, —NHCH$_2$CH$_{10}$CH$_2$CH$_2$OH, —OCH$_2$CH$_2$OCH$_2$CH$_3$, —OCH$_2$CH$_2$OCH$_2$CH$_2$OH, —NHOH, —NHCH$_3$, —NH—CH$_2$-p-C$_6$H$_4$—B(OH)$_2$, and —NHCH$_2$CH$_2$OH.

6. A gelling agent or thickener according to claim 1, wherein each of $Am_1$, $Am_2$, and $Am_3$ is based on from 1 to 12 amino acids.

7. A gelling agent or thickener according to claim 6, wherein the amino acids are chosen from the group of α-amino acids.

8. A gelling agent or thickener according to claim 7, wherein the amino acids are chosen from the group of leucine, isoleucine, lysine, valine, proline, methionine, glycine, histidine, alanine, phenylalanine, tryptophan, seine, threonine, cysteine, tyrosine, asparagine, glutamine, aspartic acid, glutamic acid, arginine, and derivatives thereof.

9. A method of gelating or thickening a solvent comprising mixing a gelling agent or thickener according to claim 1 with the solvent and triggering the mixture to obtain the thickened or gelated solvent.

10. A method of gelating or thickening a solvent comprising spraying a gelling agent or thickener according to claim 1 into the solvent in the form of a solution, or spraying the solvent into a solution of a gelling agent or thickener according to claim 1.

11. A method according to claim 10, wherein the solvent is chosen from the group of aromatic, non-aromatic hydrocarbons, alcohols, ethers, esters, aldehydes, ketones, alkanoic acids, epoxides, amines, halogenated hydrocarbons, silicon oils, vegetable oils, phosphoric acids, sulfoxides, water and mixtures thereof.

12. A method according to claim 11, wherein solvent is chosen from the group of aromatic and aliphatic hydrocarbons, alcohols, esters, halogenated hydrocarbons, ethers, vegetable oils, water, ketones and mixtures thereof.

13. A method according to claim 10, wherein the gelling agent or thickener is mixed with, or sprayed into the solvent in an amount between 0.01 and 50 wt. %, based on the weight of the resultant mixture.

14. A method according to claim 9, wherein the formation of a gel is triggered by heating of the mixture, followed by cooling.

15. A method according to claim 14, wherein the mixture is heated to a temperature of 20-200° C.

16. A method according to claim 14, wherein the mixture is cooled to a temperature in the range of from −20 to 100° C.

17. A method according to claim 9, wherein the gelling agent is mixed with the solvent under influence of sonification and the formation of a gel is triggered by stopping sonification.

18. A method according to claim 9, wherein the formation of a gel is triggered by pH, light or a chemical inducer.

19. A gel or thickened solvent obtainable by a method according to claim 9.

20. A method for transforming a thickened solvent according to claim 19 to a gel by carrying out a metathesis reaction.

21. A gel obtainable by a method according to claim 20.

22. A method for producing small particles of a drug which is essentially insoluble in water comprising dissolving the drug together with a gelling agent or thickener according to claim 1 in an organic solvent, and triggering gel formation by addition of water.

23. A method according to claim 22, wherein the organic solvent is removed from the gel by washing.

24. A method according to claim 23, wherein subsequently the gelling agent or thickener is removed.

25. A chromatographic support for chiral recognition, the support comprising a gel or thickened solvent according to claim 19 or 21.

26. A support for covalent binding of a catalyst, the support comprising a gel or thickened solvent according to claim 19 or 21.

27. A drug delivery vehicle, comprising a gel or thickened solvent according to claim 19 or 21.

28. A gelling agent or thickener according to claim 6, wherein each of $Am_1$, $Am_2$, and $Am_3$ is based on from 1 to 3 amino acids.

29. A method according to claim 15, wherein the mixture is heated to a temperature of 50-150° C.

* * * * *